(12) United States Patent
Yoshida et al.

(10) Patent No.: US 7,488,712 B2
(45) Date of Patent: Feb. 10, 2009

(54) HISTONE DEACETYLASE INHIBITORS AND METHODS FOR PRODUCING THE SAME

(75) Inventors: Minoru Yoshida, Saitama (JP); Norikazu Nishino, Fukuoka (JP); Sueharu Horinouchi, Tokyo (JP)

(73) Assignee: Kyushu Institute of Technology, Fukuoka (JP)

( * ) Notice: Subject to any disclaimer, the term of this patent is extended or adjusted under 35 U.S.C. 154(b) by 375 days.

(21) Appl. No.: 10/505,380

(22) PCT Filed: Feb. 20, 2003

(86) PCT No.: PCT/JP03/01859

§ 371 (c)(1), (2), (4) Date: Jun. 17, 2005

(87) PCT Pub. No.: WO03/070754

PCT Pub. Date: Aug. 28, 2003

(65) Prior Publication Data

US 2005/0277583 A1 Dec. 15, 2005

(30) Foreign Application Priority Data

Feb. 20, 2002 (JP) .............................. 2002-044000

(51) Int. Cl.
A61K 38/00 (2006.01)
(52) U.S. Cl. ....................................................... 514/9
(58) Field of Classification Search ....................... None
See application file for complete search history.

(56) References Cited

U.S. PATENT DOCUMENTS

| 6,399,568 B1 | 6/2002 | Nishino et al. |
| 2002/0120099 A1 | 8/2002 | Nishino et al. |
| 2003/0078369 A1* | 4/2003 | Meinke et al. .............. 530/317 |
| 2007/0185071 A1 | 8/2007 | Yoshida et al. .............. 514/184 |

FOREIGN PATENT DOCUMENTS

| CA | 2 317 003 | 8/2001 |
| EP | 1 174 438 | 1/2002 |
| EP | 1 174 438 A1 | 1/2002 |
| JP | 11-130795 | 5/1999 |
| JP | 2000-256397 | 9/2000 |
| JP | 2000256397 | 9/2000 |
| JP | 2001316283 | 11/2001 |

(Continued)

OTHER PUBLICATIONS

Rich DH, "Synthesis of dehydro amino acids and peptides by dehydrosulfenylation. Rate enhancement using sulfenic acid trapping agents," J Org Chem. Nov. 25, 1977;42(24):3815-20.*

(Continued)

*Primary Examiner*—Anish Gupta
*Assistant Examiner*—Thomas S Heard
(74) *Attorney, Agent, or Firm*—Fish & Richardson P.C.

(57) ABSTRACT

Compounds represented by formula (1) have strong inhibitory activity that is selective towards HDAC1 and HDAC4. Therefore, the compounds of the present invention are useful as pharmaceutical agents for treating or preventing diseases caused by HDAC1 and HDAC4.

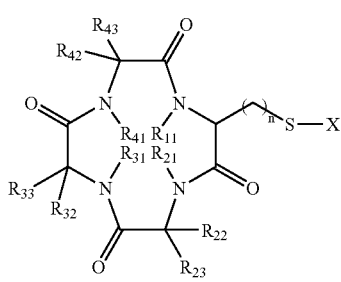

(1)

2 Claims, 8 Drawing Sheets

SCOP 148
Cyl-1 type, LDLL, C5
cyclo(-LAm7-DTyr(Me)-LIle-LPro-)

SCOP 152
Cyl-1 type, LDLD, C5
cyclo(-LAm7-DTyr(Me)-LIle-DPro-)

SCOP 149
Cyl-2 type, LDLL, C5
cyclo(-LAm7-DTyr(Me)-LIle-LPip-)

SCOP 150
Cyl-2 type, LDLD, C5
cyclo(-LAm7-DTyr(Me)-LIle-DPip-)

FOREIGN PATENT DOCUMENTS

| | | |
|---|---|---|
| JP | 2002527449 T | 8/2002 |
| JP | 2003-505417 | 2/2003 |
| JP | 2003505417 T | 2/2003 |
| WO | WO 00/21979 | 4/2000 |
| WO | WO 00/52033 | 9/2000 |
| WO | WO 01/07042 | 2/2001 |
| WO | WO 03/057722 | 7/2003 |
| WO | WO 03/070754 | 8/2003 |

OTHER PUBLICATIONS

Answer 15 of 17 HCAPLUS, two pages from search report.*
Robertson KD., "DNA methylation and chromatin—unraveling the tangled web. Oncogene," Aug. 12, 2002;21(35):5361-79.*
Bernhard et al., "Interaction between dexamethasone and butyrate in apoptosis induction: non-additive in thymocytes and synergistic in a T cell-derived leukemia cell line," *Cell Death and Differentiation*, 1999, 6(7):609-617.
Boivin et al., "Antineoplastic action of 5-aza-2'-deoxycytidine and phenylbutyrate on human lung carcinoma cells," *Anti-Cancer Drugs*, 2002, 13(8):869-874.
Cameron et al., "Synergy of demethylation and histone deacetylase inhibition in the re-expression of genes silenced in cancer," *Nature Genetics*, 1999, 21(1):103-107.
Chen et al., "Reactivation of silenced, virally transduced genes by inhibitors of histone deacetylase," *Proc. Natl. Acad. Sci. USA*, 1997, 94:5798-5803.
Coffey et al., "The Histone Deacetylase Inhibitor, CBHA, Inhibits Growth of Human Neuroblastoma Xenografts in Vivo, Alone and Synergistically with All-Trans Retinoic Acid," *Cancer Research*, 2001, 61(9):3591-3594.
Colletti et al., "Broad Spectrum Antiprotozoal Agents that Inhibit Histone Deacetylase: Structure-Activity Relatinships of Apicidin. Part 2," *Bioorganic & Medicinal Chemistry Letters*, 2001, 11:113-117.
Colletti et al, "Design and synthesis of histone deacetylase inhibitors: the development of apicidin transition state analogs," *Tetrahedron Letters*, 2000, 41:7837-7841.
Darkin-Rattray et al., "Apicidin: A novel antiprotozoal agent that inhibits parasite histone deacetylase," *Proc. Natl. Acad. Sci. USA*, 1996, 93:13143-13147.
Dhordain et al., "Corepressor SMRT binds the BTB/POZ repressing domain of the LAZ3/BCL6 oncoprotein," *Proc. Natl. Acad. Sci. USA*, 1997, 94:10762-10767.
Dion et al., "Amplification of Recombinant Adenoviral Transgene Products Occurs by Inhibition of Histone Deacetylase," *Virology*, 1997, 231:201-209.
Ferrara et al., "Histone Deacetylase-targeted Treatment Restores Retinoic Acid Signaling and Differentiation in Acute Myeloid Leukemia," *Cancer Research*, 2001, 61(1):2-7.
Finnin et al., "Structures of a histone deacetylase homologue bound to the TSA and SAHA inhibitors," *Nature*, 1999, 401:188-193.
Fischle et al., "A New Family of Human Histone Deacetylases Related to Saacharomyces cerevisiae, HDA1p," *J. Biol. Chem.*, 1999, 274(17):11713-11720.
Furumai et al., "Potent histone deacetylase inhibitors built from trichostatin A and cyclic tetrapeptide antibiotics including trapoxin," *Proc. Natl. Acad. Sci. USA*, 2001, 98(1):87-92.
Furumai et al., "FK228 (Depsipeptide) as a Natural Prodrug That Inhibits Class I Histone Deacetylases," *Cancer Research*, 2002, 62(17):4916-4921.
Göttlicher et al., "Valproic acid defines a novel class of HDAC inhibitors inducing differentiation of transformed cells," *EMBO J.*, 2001, 20(24):6969-6978.
Grignani et al., "Fusion proteins of the retinoic acid receptor-α recruit histone deacetylase in promyelocytic leukaemia," *Nature*, 1998, 391:815-818.
He et al., "Distinct interactions of PML-RARα and PLZF-RARα with co-repressors determine differential responses to RA in APL," *Nature Genetics*, 1998, 18:126-134.

Hoshikawa et al., "Expression of Differentiation-related Markers in Teratocarcinoma Cells via Histone Hyperacetylation by Trichostatin A," *Agric. Biol. Chem.*, 1991, 55(6):1491-1495.
Hubbert et al., "HDAC6 is a microtubule-associated deacetylase," *Nature*, 2002, 417:455-458.
Inokoshi et al., "Neuronal Differentiation of Neuro 2a Cells by Inhibitors of Cell Cycle Progression, Trichostatin A and Butyrolactone I," *Biochem. Biophys. Res. Comm.*, 1999, 256(2):372-376.
Ito et al., "p300/CBP-mediated p53 acetylation is commonly induced by p53-activating agents and inhibited by MDM2," *EMBO J.*, 2001, 20(6):1331-1340.
Juan et al., "Histone Deacetylases Specifically Down-regulate p53-dependent Gene Activation," *J. Biol. Chem.*, 2000, 275(27):20436-20443.
Kim et al., "Oxamflatin is a novel antitumor compound that inhibits mammalian histone deacetylase," *Oncogene*, 1999, 18:2461-2470.
Kim et al., "Histone deacetylases induce angiogenesis by negative regulation of tumor suppressor genes," *Nature Medicine*, 2001, 7(4):437-443.
Komatsu et al., "Cyclic Hydroxamic-acid-containing Peptide 31, a Potent Synthetic Histone Deacetylase Inhibitor with Antitumor Activity," *Cancer Research*, 2001, 61(11):4459-4466.
Kwon et al., "Histone Deacetylase Inhibitor FK228 Inhibits Tumor Angiogenesis," *Int. J. Cancer*, 2002, 97:290-296.
Li et al., "Casual Relationship between the Loss of RUNX3 Expression and Gastric Cancer," *Cell*, 2002, 109(1):113-124.
Lin et al., "Role of the histone deacetylase complex in acute promyelocytic leukaemia," *Nature*, 1998, 391:811-814.
Marks et al., "Histone Deacetylase Inhibitors: Inducers of Differentiation or Apoptosis of Transformed Cells," *J. Natl. Cancer Inst.*, 2000, 92:1210-1216.
Matsuyama et al., "In vivo destabilization of dynamic microtubules by HDAC6-mediated deacetylation," *EMBO J.*, 2002, 21(24):6820-6831.
Meinke et al., "Synthesis of side chain modified apicidin derivatives: potent mechanism-based histone deacetylase inhibitors," *Tetrahedron Letters*, 2000, 41:7831-7835.
McKinsey et al., "Signal-dependent nuclear export of a histone deacetylase regulates muscle differentiation," *Nature*, 2000, 408:106-111.
Minucci et al., "A histone deacetylase inhibitor potentiates retinoid receptor action in embryonal carcinoma cells," *Proc. Natl. Acad. Sci. USA*, 1997, 94(21):11295-11300.
Munster et al., "The Histone Deacetylase Inhibitor Suberoylanilide Hydroxamic Acid Induces Differentiation of Human Breast Cancer Cells," *Cancer Research*, 2001, 61(23):8492-8497.
Nakajima et al., "FR901228, a Potent Antitumor Antibiotic, Is a Novel Histone Deacetylase Inhibitor," *Exp. Cell Res.*, 1998, 241(1):126-133.
Nan et al., "Transcriptional repression by the methyl-CpG-binding protein MeCP2 involves a histone deacetylase complex," *Nature*, 1998, 393(6683):386-389.
Petti et al., "Complete remission through blast cell differentiation in PLZF/RARα-positive acute promyelocytic leukemia: in vitro and in vivo studies," *Blood*, 2002, 100(3):1065-1067.
Primeau et al., "Synergistic Antineoplastic Action of DNA Methylation Inhibitor 5-AZA-2'-Deoxycytidine and Histone Deacetylase Inhibitor Depsipeptide on Human Breast Carcinoma Cells," *Int. J. Cancer*, 2003, 103:177-184.
Saito et al., "A synthetic inhibitor of histone deacetylase, MS-27-275, with marked in vivo antitumor activity against human tumors," *Proc. Natl. Acad. Sci. USA*, 1999, 96(8):4592-4597.
Verdel and Khochbin, "Identification of a New Family of Higher Eukaryotic Histone Deacetylases," *J. Biol. Chem.*, 1999, 274(4):2440-2445.
Verdel et al., "Active maintenance of mHDA2/mHDAC6 histone-deacetylase in the cytoplasm," *Current Biology*, 2000, 10:1-3.
Wang et al., "Inhibitors of Histone Deacetylase Relieve ETO-mediated Repression and Induce Differentiation of AML1-ETO Leukemia Cells," *Cancer Research*, 1999, 59(12):2766-2769.

Yang et al., "Isolation and Characterization of cDNAs Corresponding to an Additional Member of the Human Histone Deacetylase Gene Family," *J. Biol. Chem.*, 1997, 272(44):28001-28007.

Yoshida et al., "Potent and Specific Inhibition of Mammalian Histone Deacetylase Both in Vivo and in Vitro by Trichostatin A," *J. Biol. Chem.*, 1990, 265(28):17174-17179.

Yoshida et al., "Trichostatin A and trapoxin : novel chemical probes for the role of histone acetylation in chromatin structure and function," *BioEssays*, 1995, 17(5):423-430.

Yoshida et al., "Effects of Trichostatins on Differentiation of Murine Erythroleukemia Cells," *Cancer Research*, 1987, 47(14):3688-3691.

De Schepper et al., "Inhibition of Histone Deacetylases by Chlamydocin Induces Apoptosis and Proteasome-Mediated Degradation of Survivin," *J. Pharmacol. Exp. Ther.*, 2003, 304(2):881-888.

Jose et al., "Toward an HDAC6 inhibitor: synthesis and conformational analysis of cyclic hexapeptide hydroxamic acid designed from α-tubulin sequence," *Bioorg. Med. Chem.*, 2004, 12:1351-1356.

Mori et al., "FR235222, a Fungal Metabolite, is a Novel Immunosuppressant that Inhibits Mammalian Histone Deacetylase (HDAC). I. Taxonomy, Fermentation, Isolation and Biological Activities," *J. Antibiot.*, 2003, 56(2):72-79.

Nishino et al., "Synthesis and histone deacetylase inhibitory activity of cyclic tetrapeptides containing a retrohydroxamate as zinc ligand," *Bioorg. Med. Chem. Lett.*, 2004, 14:2427-2431.

Yoshida et al., "Potent and Specific Inhibition of Mammalian Histone Deacetylase Both in Vivo and in Vitro by Trichostatin A," *J. Biol. Chem.*, 1990, 265(28):17174-17179.

Minako Hoshi et al., "Activation of a $Ca^{2+}$—inhibitable Protein Kinase That Phosphorylates Microtubule-associated Protein 2 in Vitro by Growth Factors, Phorbol Esters, and Serum in Quiescent Cultured Human Fibroblasts," *The Journal of Biological Chemistry*, vol. 263, No. 11 (Apr. 15, 1988) pp. 5396-5401.

William Scherer et al., "Studies on the Propagation in Vitro of Poliomyelitis Viruses: IV," *The Journal of Experimental Medicine*, vol. 97 (1953) pp. 695-710.

\* cited by examiner

SCOP 304
HOMODIMER OF SCOP 152

SCOP 152
Cyl-1 type, LDLD, C5
cyclo(-LAm7-DTyr(Me)-LIle-DPro-)

HISTONE DEACETYLASE INHIBITORS AND METHODS FOR PRODUCING THE SAME

CROSS-REFERENCE TO RELATED APPLICATIONS

This application is a National Stage application under 35 U.S.C. §371 and claims the benefit under 35 U.S.C. §119(a) of International Application No. PCT/JP03/01859 having an International Filing Date of Feb. 20, 2003, which claims the benefit of priority of Japanese Application Ser. No. 2002-44000 having a filing date of Feb. 20, 2002, both of which are incorporated herein in their entirety.

TECHNICAL FIELD

The present invention relates to histone deacetylase (HDAC) inhibitors and methods for producing the same.

BACKGROUND ART

Eukaryotic chromatin structure and gene expression are regulated by histone acetylation by histone acetyltransferase (HAT), and deacetylation by histone deacetylase (HDAC). HDAC inhibitors are already known to induce cancer cell differentiation and apoptosis, and are expected to be useful as antitumor agents (Marks, P. A., Richon, V. M., and Rifkind, R. A. (2000). Histone deacetylase inhibitors: Inducers of differentiation or apoptosis of transformed cells. J. Natl. Cancer Inst. 92, 1210-1216; Yoshida, M., Horinouchi, S., and Beppu, T. (1995). Trichostatin A and trapoxin: novel chemical probes for the role of histone acetylation in chromatin structure and function. Bioessays 17, 423-430; Bernhard, D., Löffler, M., Hartmann, B. L., Yoshida, M., Kofler, R., and Csordas, A. (1999). Interaction between dexamethasone and butyrate in apoptosis induction: non-additive in thymocytes and synergistic in a T cell-derived leukemia cell line. Cell Death Diff. 6, 609-607).

In fact, clinical studies have begun in the United States for some HDAC inhibitors (Nakajima, H., Kim, Y. B., Terano, H., Yoshida, M., and Horinouchi, S. (1998). FR901228, a potent antitumor antibiotic, is a novel histone deacetylase inhibitor. Exp. Cell Res. 241, 126-133; Saito, A., Yamashita, T., Mariko, Y., Nosaka, Y., Tsuchiya, K., Ando, T., Suzuki, T., Tsuruo, T., and Nakanishi, O. (1999). A synthetic inhibitor of histone deacetylase, MS-27-275, with marked in vivo antitumor activity against human tumors. Proc. Natl. Acad. Sci. USA 96, 4592-4597) that are effective as antitumor agents in animal experiments.

Tricostatin A (TSA) is well known as a specific HDAC inhibitor (Yoshida, M., Kijima, M., Akita, M., and Beppu, T. (1990). Potent and specific inhibition of mammalian histone deacetylase both in vivo and in vitro by trichostatin A. J. Biol. Chem. 265, 17174-17179). Actually, TSA has been known to induce differentiation to leukemia cells, neuronal cells, breast cancer cells, and the like (Yoshida, M., Nomura, S., and Beppu, T. Effects of trichostatins on differentiation of murine erythroleukemia cells. Cancer Res. 47: 3688-3691, 1987; Hoshikawa, Y., Kijima, M., Yoshida, M., and Beppu, T. Expression of differentiation-related markers in teratocarcinoma cells via histone hyperacetylation by trichostatin A. Agric. Biol. Chem. 55: 1491-1495, 1991; Minucci, S., Horn, V., Bhattacharyya, N., Russanova, V., Ogryzko, V. V., Gabriele, L., Howard, B. H., and Ozato, K. A histone deacetylase inhibitor potentiates retinoid receptor action in embryonal carcinoma cells. Proc. Natl. Acad. Sci. USA 94: 11295-11300, 1997; Inokoshi, J., Katagiri, M., Arima, S., Tanaka, H., Hayashi, M., Kim, Y. B., Furumai, R., Yoshida, M., Horinouchi, S., and Omura, S. (1999). Neuronal differentiation of Neuro 2a cells by inhibitors of cell progression, trichostatin A and butyrolactone I. Biochem. Biophys. Res. Commun. 256, 372-376; Wang, J., Saunthararajah, Y., Redner, R. L., and Liu, J. M. Inhibitors of histone deacetylase relieve ETO-mediated repression and induce differentiation of AML1-ETO leukemia cells. Cancer Res. 59: 2766-2769, 1999; Munster, P. N., Troso-Sandoval, T., Rosen, N., Rifkind, R., Marks, P. A., and Richon, V. M. The histone deacetylase inhibitor suberoylanilide hydroxamic acid induces differentiation of human breast cancer cells. Cancer Res. 61: 8492-8497, 2001; Ferrara, F. F., Fazi, F., Bianchini, A., Padula, F., Gelmetti, V., Minucci, S., Mancini, M., Pelicci, P. G., Lo Coco, F., and Nervi, C. Histone deacetylase-targeted treatment restores retinoic acid signaling and differentiation in acute myeloid leukemia. Cancer Res. 61: 2-7, 2001; Gottlicher, M., Minucci, S., Zhu, P., Kramer, O. H., Schimpf, A., Giavara, S., Sleeman, J. P., Lo Coco, F., Nervi, C., Pelicci, P. G., and Heinzel, T. Valproic acid defines a novel class of HDAC inhibitors inducing differentiation of transformed cells. EMBO J. 20: 6969-6978, 2001). Furthermore, the TSA activities of differentiation induction and apoptosis induction are known to synergistically increase when used in combination with drugs which activate gene expression by mechanisms different to HDAC inhibitors. For example, cancer cell differentiation is promoted by using HDAC inhibitors in combination with retinoic acids, which activate retinoic acid receptors that serve as nuclear receptors, inducing gene expression relevant to differentiation (Minucci, S., Horn, V., Bhattacharyya, N., Russanova, V., Ogryzko, V. V., Gabriele, L., Howard, B. H., and Ozato, K. A histone deacetylase inhibitor potentiates retinoid receptor action in embryonal carcinoma cells. Proc. Natl. Acad. Sci. USA 94: 11295-11300, 1997; Ferrara, F. F., Fazi, F., Bianchini, A., Padula, F., Gelmetti, V., Minucci, S., Mancini, M., Pelicci, P. G., Lo Coco, F., and Nervi, C. Histone deacetylase-targeted treatment restores retinoic acid signaling and differentiation in acute myeloid leukemia. Cancer Res. 61: 2-7, 2001; Coffey, D. C., Kutko, M. C., Glick, R. D., Butler, L. M., Heller, G., Rifkind, R. A., Marks, P. A., Richon, V. M., and La Quaglia, M. P. The histone deacetylase inhibitor, CBHA, inhibits growth of human neuroblastoma xenografts in vivo, alone and synergistically with all-trans retinoic acid. Cancer Res. 61: 3591-3594, 2001; Petti, M. C., Fazi, F., Gentile, M., Diverio, D., De Fabritiis, P., De Propris, M. S., Fiorini, R., Spiriti, M. A., Padula, F., Pelicci, P. G., Nervi, C., and Lo Coco, F. Complete remission through blast cell differentiation in PLZF/RARalpha-positive acute promyelocytic leukemia: in vitro and in vivo studies. Blood 100: 1065-1067, 2002). 5-azadeoxycytidine inhibits DNA methylation to reduce expression of tumor suppressor genes in many cancer cells. TSA used in combination with 5-azadeoxycytidine promotes cancer cell apoptosis and restoration of tumor-suppressing gene expression (Nan, X., Ng, H. H., Johnson, C. A., Laherty, C. D., Turner, B. M., Eisenman, R. N., and Bird, A. Transcriptional repression by deacetylase complex. Nature 393: 386-389, 1998; Cameron, E. E., Bachman, K. E., Myohanen, S., Herman, J. G., and Baylin, S. B. Synergy of demethylation and histone deacetylase inhibition in the re-expression of genes silenced in cancer. Nature Genet. 21: 103-107, 1999; Li, Q. L., Ito, K., Sakakura, C., Fukamachi, H., Inoue, K., Chi, X. Z., Lee, K. Y., Nomura, S., Lee, C. W., Han, S. B., Kim, H. M., Kim, W. J., Yamamoto, H., Yamashita, N., Yano, T., Ikeda, T., Itohara, S., Inazawa, J., Abe, T., Hagiwara, A., Yamagishi, H., Ooe, A., Kaneda, A., Sugimura, T., Ushijima, T., Bae, S. C., and Ito, Y. Causal relationship between the loss of RUNX3 expression and gastric cancer. Cell 109: 113-124, 2002; Boivin, A. J., Momparler, L. F., Hurtubise, A., and Momparler, R. L. Antineoplastic action of 5-aza-2'-deoxycytidine and phenylbutyrate on human lung carcinoma cells. Anticancer Drugs 13: 869-874, 2002; Primeau, M., Gagnon, J., and Momparler, R. L. Synergistic antineoplastic action of DNA methylation inhibitor 5-AZA-2'-deoxycytidine and histone deacetylase inhibitor depsipeptide on human breast carcinoma cells. Int J Cancer 103: 177-184, 2003).

HDAC inhibitors are expected to be not only antitumor agents but also cancer preventives. TSA, SAHA, and the like significantly suppressed the occurrence of breast cancer induced in animal models. Also, investigations carried out using valproic acids indicated that HDAC inhibitors suppress metastasis (Gottlicher, M., Minucci, S., Zhu, P., Kramer, O. H., Schimpf, A., Giavara, S., Sleeman, J. P., Lo Coco, F., Nervi, C., Pelicci, P. G., and Heinzel, T. Valproic acid defines a novel class of HDAC inhibitors inducing differentiation of transformed cells. EMBO J. 20: 6969-6978, 2001).

HDAC inhibitors are used not only as tumor suppressive agents, but also, for example, as agents for treating and improving autoimmune diseases, skin diseases, infectious diseases, and such (Darkin-Rattray et al. Proc. Natl. Acad. Sci. USA 93, 13143-13147, 1996), as well as in improving the efficiency of vector introduction in gene therapy (Dion et al., Virology 231, 201-209, 1997), promoting the expression of introduced genes (Chen et al., Proc. Natl. Acad. Sci. USA 94, 5798-5803, 1997), and the like. Furthermore, HDAC inhibitors are presumed to have angiogenesis-inhibiting functions (Kim, M. S., Kwon, H. J., Lee, Y. M., Baek, J. H., Jang, J. E., Lee, S. W., Moon, E. J., Kim, H. S., Lee, S. K., Chung, H. Y., Kim, C. W., and Kim, K. W. (2001). Histone deacetylases induce angiogenesis by negative regulation of tumor suppressor genes. Nature Med. 7, 437-443; Kwon, H. J., Kim, M. S., Kim, M. J., Nakajima, H., and Kim, K. W. (2002). Histone deacetylase inhibitor FK228 inhibits tumor angiogenesis. Int. J. Cancer 97, 290-296).

Ten or more HDAC subtypes exist, and recently, specific HDAC subtypes have been identified as being closely related to cancers. For example, it has been discovered that acetylation of the tumor suppressor gene p53, which plays an extremely important role in suppressing carcinogenesis, is very important in the functional expression of p53 itself (Ito, A., Lai, C. H., Zhao, X., Saito, S., Hamilton, M. H., Appella, E., and Yao, T. P. (2001). p300/CBP-mediated p53 acetylation is commonly induced by p53-activating agents and inhibited by MDM2. EMBO J. 20, 1331-1340), and HDAC1 and HDAC2 are involved in the inhibition of p53 function (Juan, L. J., Shia, W. J., Chen, M. H., Yang, W. M., Seto, E., Lin, Y. S., and Wu, C. W. (2000). Histone Deacetylases Specifically Down-regulate p53-dependent Gene Activation. J. Biol. Chem. 275, 20436-20443). It has also been discovered that proteins PML-RAR and PLZF-RAR, involved in the onset of promyelocytic leukemia (APL), and oncogenes such as Bcl-6, which is involved in the onset of lymphomas, recruit HDAC4 or such via nuclear co-repressors, and suppress expression of the gene group necessary for normal differentiation, causing carcinogenesis (Dhordain P., Albagli, O., Lin, R. J., Ansieau, S., Quief, S., Leutz, A., Kerckaert, J. P., Evans, R. M., and Leprince, D. (1997). Corepressor SMRT binds the BTB/POZ repressing domain of the LAZ3/BCL6 oncoprotein. Proc. Natl. Acad. Sci. USA 94, 10762-10767; Grignani, F., De, M. S., Nervi, C., Tomassoni, L., Gelmetti, V., Cioce, M., Fanelli, M., Ruthardt, M., Ferrara, F. F., Zamir, I., Seiser, C., Grignani, F., Lazar, M. A., Minucci, S., and Pelicci, P. G. (1998). Fusion proteins of the retinoic acid receptor-alpha recruit histone deacetylase in promyelocytic leukaemia. Nature 391, 815-818; He, L. Z., Guidez, F., Tribioli, C., Peruzzi, D., Ruthardt, M., Zelent, A., and Pandolfi, P. P. (1998). Distinct interactions of PML-RARalpha and PLZF-RARalpha with co-repressors determine differential responses to RA in APL. Nature Genet. 18, 126-135; Lin, R. J., Nagy, L., Inoue, S., Shao, W., Miller, W. J., and Evans, R. M. (1998). Role of the histone deacetylase complex in acute promyelocytic leukaemia. Nature 391, 811-814). On the other hand, HDAC subtypes which play a very important role in the development and differentiation of normal tissues are known to exist among those HDAC subtypes with tissue-specific expression (McKinsey, T. A., Zhang, C. L., Lu, J., and Olson, E. N. (2000). Signal-dependent nuclear export of a histone deacetylase regulates muscle differentiation. Nature 408, 106-111; Verdel, A., and Khochbin, S. (1999). Identification of a new family of higher eukaryotic histone deacetylases. Coordinate expression of differentiation-dependent chromatin modifiers. J. Biol. Chem. 274, 2440-2445). In order to avoid inhibition of these HDACs, development of a subtype-specific inhibitor is thought to be necessary.

HDAC6 is an enzyme which is shuttled between the nucleus and the cytoplasm by nucleo-cytoplasmic transport, and which normally locates in the cytoplasm (Verdel, A., Curtet, S., Brocard, M. -P., Rousseaux, S., Lemercier, C., Yoshida, M., and Khochbin, S. (2000). Active maintenance of mHDA2/mHDAC6 histone-deacetylase in the cytoplasm. Curr. Biol. 10, 747-749). HDAC6 is highly expressed in the testes, and is presumed to relate to the differentiation of normal tissues. Furthermore, HDAC6 is known to be associated with microtubule deacetylation, and to control microtubule stability (Matsuyama, A., Shimazu, T., Sumida, Y., Saito, A., Yoshimatsu, Y., Seigneurin-Berny, D., Osada, H., Komatsu, Y., Nishino, N., Khochbin, S., Horinouchi, S., and Yoshida, M. (2002). In vivo destabilization of dynamic microtubules by HDAC6-mediated deacetylation. EMBO J. 21, 6820-6831). HDAC6 is also a deacetylation enzyme bonded to a microtubule and affecting cell mobility (Hubbert, C., Guardiola, A., Shao, R., Kawaguchi, Y., Ito, A., Nixon, A., Yoshida, M., Wang, X. -F., and Yao, T. -P. (2002). HDAC6 is a microtubule-associated deacetylase. Nature 417, 455-458). Accordingly, HDAC6 inhibitors may be metastasis-suppressing agents. TSA inhibits each HDAC subtype to about the same degree. However, HDAC6 cannot be inhibited by trapoxins comprising cyclic tetrapeptide structure and epoxyketone as active groups (Furumai, R., Komatsu, Y., Nishino, N., Khochbin, S., Yoshida, M., and Horinouchi, S. Potent histone deacetylase inhibitors built from trichostatin A and cyclic tetrapeptide antibiotics including trapoxin. Proc. Natl. Acad. Sci. USA 98: 87-92, 2001). Based on the information on the three-dimensional structure of the enzyme, trapoxins are assumed to exert poor binding properties to HDAC6 due to the structure of its cyclic tetrapeptide moiety that interacts with the weakly conserved outward surface of the enzyme active center. This implies that altering the cyclic tetrapeptide portion may result in inhibitors that are selective for a variety of HDAC.

TSA shows inhibition activity due to the coordination of its hydroxamic acid group with zinc in the HDAC active pocket (Finnin, M. S., Donigian, J. R., Cohen, A., Richon, V. M., Rifkind, R. A., Marks, P. A., Breslow, R., and Pavletich, N. P. Structures of a histone deacetylase homologue bound to the TSA and SAHA inhibitors. Nature 401: 188-193, 1999). Examples of known HDAC inhibitors comprising hydroxamic acid are Oxamflatin (Kim, Y. B., Lee, K. -H., Sugita, K., Yoshida, M., and Horinouchi, S. Oxamflatin is a novel antitumor compound that inhibits mammalian histone deacetylase. Oncogene 18: 2461-2470, 1999) and CHAP (Furumai, R., Komatsu, Y., Nishino, N., Khochbin, S., Yoshida, M., and Horinouchi, S. Potent histone deacetylase inhibitors built from trichostatin A and cyclic tetrapeptide antibiotics including trapoxin. Proc. Natl. Acad. Sci. USA 98: 87-92, 2001., Komatsu, Y., Tomizaki, K. -y., Tsukamoto, M., Kato, T., Nishino, N., Sato, S., Yamori, T., Tsuruo, T., Furumai, R., Yoshida, M., Horinouchi, S., and Hayashi, H. Cyclic Hydroxamic-acid-containing Peptide 31, a potent synthetic histone deacetylase inhibitor with antitumor activity. Cancer Res. 61: 4459-4466, 2001). However, since TSA is instable in blood and has a strong hydroxamic acid chelating function, it chelates with other essential metal ions, and therefore, HDAC inhibitors comprising hydroxamic acid have not actually been used as antitumor agents to date. Meanwhile, thiol groups produced by the reduction of FK228 disulfide bonds have recently been shown to serve as active groups to be coordinated with zinc in the HDAC active pocket, inhibiting HDAC. Thus, FK228 is a prodrug that is activated when reduced by cellular reducing activity (Furumai, R., Matsuyama, A., Kobashi, N., Lee, K. -H., Nishiyama, M., Nakajima, H., Tanaka, A., Komatsu, Y., Nishino, N., Yoshida, M., and Horinouchi, S. (2002). FK228 (depsipeptide) as a natural prodrug that inhibits class I histone deacetylases. Cancer Res. 62, 4916-4921).

Furthermore, a number of HDAC inhibitors comprising cyclic tetrapeptide structures and epoxyketones as active groups have been isolated from natural environments. On the basis of such findings, the cyclic tetrapeptide structure is suggested to be useful in enzyme identification (as described above, Yoshida, et al., 1995), however, from various viewpoints such as stability, existing inhibitors have not advanced to the level of being satisfactorily qualified as pharmaceutical products. Therefore, production of pharmaceutical agents in which these problematic points have been resolved is strongly anticipated.

DISCLOSURE OF THE INVENTION

The present inventors aim to provide novel HDAC inhibitors comprising a cyclic tetrapeptide structure, and methods for producing the same.

In consideration of the above-mentioned objectives, the inventors of the present invention synthesized compounds comprising cyclic tetrapeptide structures that comprise thiol groups and their disulfide bonds, and then analyzed the HDAC inhibition activity of these compounds. As a result, it was found that compounds comprising disulfide bonds did not exhibit very high HDAC inhibition activity against enzymes in vitro. However, when converted into thiols by coexisting with the reducing agent dithiothreitol, they showed strong HDAC inhibition activity. On the other hand, the intracellular level of disulfide activity was observed to be as high as that of TSA and thiols. Accordingly, disulfides were shown to be useful as prodrugs for HDAC inhibitors, in which the disulfide bonds are cleaved by intracellular reduction after being taken up into cells, inducing strong activity. Furthermore, the compounds were found to be more stabile in the serum when the thiol groups were protected in such a manner, and it was discovered that by binding the protection groups (-SX) with various functional compounds, the compounds could bind to compounds with desired activities, other than HDAC inhibitors.

The invention relates to HDAC inhibitors and methods for producing the same, and specifically provides the following [1] to [9]:

[1] A compound represented by the following formula (1):

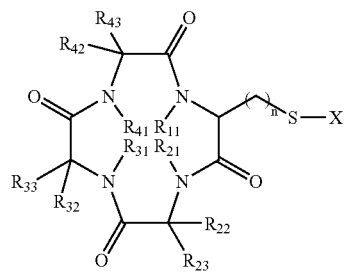

(1)

[wherein, $R_{11}$, $R_{21}$, $R_{31}$, and $R_{41}$ independently denote hydrogen or methyl; $R_{22}$, $R_{23}$, $R_{32}$, $R_{33}$, $R_{42}$, and $R_{43}$ independently denote a hydrogen, a linear alkyl with one to six carbon atoms, a linear alkyl with one to six carbon atoms to which a non-aromatic cyclic alkyl group or substituted or unsubstituted aromatic ring, a non-aromatic cyclic alkyl, or a non-aromatic cyclic alkyl group to which a non-aromatic cyclic alkyl group or a substituted or unsubstituted aromatic ring is bound; the pairs of $R_{21}$ and $R_{22}$, $R_{22}$ and $R_{23}$, $R_{31}$ and $R_{32}$, $R_{32}$ and $R_{33}$, $R_{41}$, and $R_{42}$, and $R_{42}$ and $R_{43}$ independently denote acyclic structures without binding or cyclic structures by binding through a linear alkylene group with a one- to five-carbon main chain, a linear alkylene group with a one- to five-carbon main chain comprising a branched chain with a one to six carbons, or a linear alkylene group with a one- to five-carbon main chain comprising a ring structure of one to six carbons; X denotes hydrogen, a structure identical to that shown to the left of X, a substituted or unsubstituted alkyl or aryl group in any structure comprising a sulfur atom capable of binding with the sulfur atom in formula (1) through a disulfide bond, or a sulfur atom binding with the sulfur atom bonded to the terminus of $R_{22}$, $R_{23}$, $R_{32}$, $R_{33}$, $R_{42}$, or $R_{43}$, and located to the left of X, via an intramolecular disulfide bond].

[2] A histone deacetylase inhibitor that comprises the compound of [1] as an active ingredient.

[3] An apoptosis inducing agent that comprises the compound of [1] as an active ingredient.

[4] A differentiation-inducing agent that comprises the compound of [1] as an active ingredient.

[5] An angiogenesis inhibitor that comprises the compound of [1] as an active ingredient.

[6] An anti-metastatic agent comprising the compound of [1] as an active ingredient.

[7] A pharmaceutical agent for treating or preventing a disease caused by histone deacetylase 1 or 4, comprising the compound of [1] as an active ingredient.

[8] The pharmaceutical agent of [7], wherein the disease caused by histone deacetylase 1 or 4 is cancer, autoimmune disease, skin disease, or infectious disease.

[9] A method for producing the compound of [1], which comprises the steps of:

reacting a compound represented by formula (2)

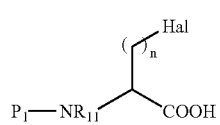

(2)

(wherein, n is same as that defined in formula (1); Hal denotes a halogen atom selected from a chlorine atom, bromine atom, or iodine atom, or an allyl or alkylsulfoxy group useful for a free group; $P_2$ denotes a protection group for an amino group);

with a compound represented by formula (3).

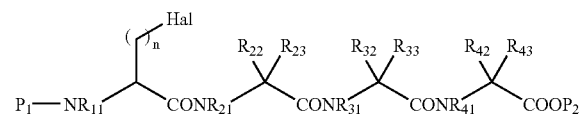

(3)

(wherein $R_{11}$, $R_{21}$, $R_{22}$, $R_{23}$, $R_{31}$, $R_{32}$, $R_{33}$, $R_{41}$, $R_{42}$, and $R_{43}$ are same as defined in formula (1); $P_2$ denotes a protection group for a carboxyl group);

in the presence of a peptide-bonding agent to obtain a compound represented by formula (4)

(4)

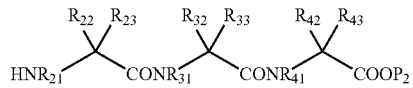

(wherein n, $R_{11}$, $R_{21}$, $R_{22}$, $R_{23}$, $R_{31}$, $R_{32}$, $R_{33}$, $R_{41}$, $R_{42}$, $R_{43}$, $P_1$, $P_2$, and Hal are the same as defined above);

subjecting the compound represented by formula (4) to catalytic hydrogenation, acid treatment, or hydrolysis to remove $P_1$ and $P_2$;

and then subjecting to cyclization in the presence of a peptide-bonding agent to obtain a compound represented by formula (5)

(5)

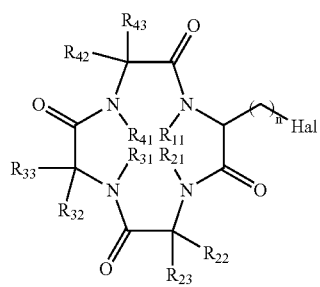

(wherein n, $R_{11}$, $R_{21}$, $R_{22}$, $R_{23}$, $R_{31}$, $R_{32}$, $R_{33}$, $R_{41}$, $R_{42}$, $R_{43}$, $P_1$, $P_2$, and Hal are the same as defined above);

or reacting a compound represented by formula (6)

(6)

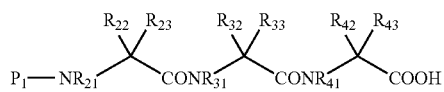

(wherein $R_{21}$, $R_{22}$, $R_{23}$, $R_{31}$, $R_{32}$, $R_{33}$, $R_{41}$, $R_{42}$, R43, and $P_1$ are the same as defined above);

with a compound represented by formula (7)

(7)

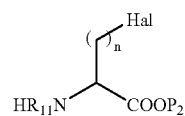

(wherein n, $R_{11}$, $P_2$, and Hal are the same as defined above);

in the presence of a peptide-bonding agent to obtain a compound represented by formula (8)

(8)

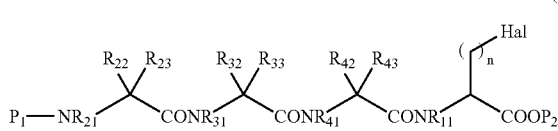

(wherein n, $R_{11}$, $R_{21}$, $R_{22}$, $R_{23}$, $R_{31}$, $R_{32}$, $R_{33}$, $R_{41}$, $R_{42}$, $R_{43}$, $P_1$, $P_2$, and Hal are the same as defined above);

subjecting the compound represented by formula (8) to catalytic hydrogenation, acid treatment, fluoride anion treatment, or hydrolysis to remove $P_1$ and $P_2$;

and then subjecting to cyclization in the presence of a peptide-bonding agent to obtain the compound represented by formula (5);

following, for both process, the steps of:

reacting the compound represented by formula (5) with a reagent comprising sulfur atoms to obtain a compound represented by formula (9)

(9)

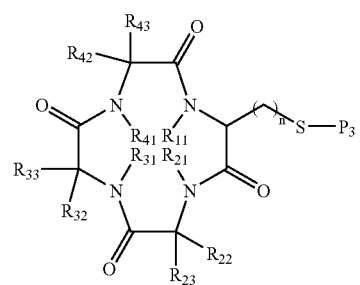

(wherein n, $R_{11}$, $R_{21}$, $R_{22}$, $R_{23}$, $R_{31}$, $R_{32}$, $R_{33}$, $R_{41}$, $R_{42}$, and $R_{43}$ are the same as defined above; $P_3$ denotes a protection group for sulfohydryl group); and then treating the compound represented by formula (9) with an oxidizing agent as well as ammonia or another amine.

Hereinafter, modes for carrying out the present invention will be specifically described with reference to drawings.

The compounds of the present invention can be defined by the above-mentioned formula (1). Such compounds can be used as the HDAC inhibitors.

In the above-mentioned formula (1), $R_{11}$, $R_{21}$, $R_{31}$, and $R_{41}$ may each independently be hydrogen or methyl. $R_{22}$, $R_{23}$, $R_{32}$, $R_{33}$, $R_{42}$, and $R_{43}$ may each independently be hydrogen, a linear alkyl with one to six carbon atoms, or a non-aromatic cyclic alkyl group, in which the linear alkyl group with one to six carbon atoms and the non-aromatic cyclic alkyl group may bind with a non-aromatic cyclic alkyl group, or substituted or unsubstituted aromatic ring. Pairs of $R_{21}$ and $R_{22}$, $R_{22}$ and $R_{23}$, $R_{31}$ and $R_{32}$, $R_{32}$ and $R_{33}$, $R_{41}$ and $R_{42}$, and $R_{42}$ and $R_{43}$ can each independently be in an acyclic structure without binding, or may bind through a linear alkylene group with a one- to five-carbon main chain, a linear alkylene group with a one- to five-carbon main chain comprising a branched chain with one to six carbons, or a linear alkylene group with a one- to five-carbon main chain comprising a ring structure of one to six carbons. Since the cyclic tetrapeptide structure portion is thought to function as a cap to seal a pocket of HDAC, this cap structure can be arbitrarily selected from the above-mentioned linear alkyl with one to six carbon atoms, aromatic cyclic alkyl, and aromatic groups that can substitute for them.

Furthermore, hydrogen can be used as X in formula (1) to directly form a thiol group with a neighboring sulfur atom that exhibits HDAC inhibition activity. However, if the thiol group formed by using a hydrogen as X is exposed, the resulting compound becomes unstable in vivo. Therefore, if X is a hydrogen, the present compounds are preferably combined with a means for their stable delivery to a desired site, such as a drug delivery system. In order to enhance the stability of thiol groups comprising HDAC inhibition activity, it is preferable that X is a substituent group which is metabolized in vivo and harmless in the living body. This kind of substituent group is preferably a group comprising a sulfur atom capable of forming a disulfide bond with the sulfur atom next to the X, and can be a group that itself shows some efficacy, and can also be a group that functions simply as a protective group. Such a substituent group comprising a sulfur atom can be:

a structure identical to that shown to the left of X; an alkyl group or aryl group in any structure comprising a sulfur atom capable of binding via a disulfide bond with the sulfur atom in the above-mentioned formula (1); or a sulfur atom binding with the sulfur atom bonded to the terminus of the above-mentioned $R_{22}$, $R_{23}$, $R_{32}$, $R_{33}$, $R_{42}$, or $R_{43}$ and located to the left of X via an intra-molecular disulfide bond. In this case, if the substituent group has the same structure as that to the left of X, resulting in a dimer structure, the disulfide bond is cut by in vivo metabolism to isolate an HDAC inhibitor comprising the activity of two molecules. Furthermore, any alkyl or aryl comprising a sulfur atom may have further substituted groups, or may be a structure capable of exhibiting an effect identical to or different from that of the HDAC inhibitor.

Examples of the SS-hybrid X atom groups of the present invention are alkylmercaptans such as methylmercaptan, benzylmercaptan and cyclohexylmercaptan and aromatic mercaptans such as thiophenol and mercaptopyridine, as well as alkylmercaptans and allylmercaptans in which a portion of the atom groups in the structure of natural physiologically active substances, such as 5-azadeoxycytidine and retinoic acid, are substituted with thiol groups. Preferable examples are methylmercaptan, ethylmercaptan, mercaptoethanol, cysteamine, cysteine, thiophenol, 2-mercaptopyridine, 4-mercaptopyridine, 5'-mercapto-5-azadoxycytidine, 3'-mercapto-5-azadeoxycytidine, and thioretinol.

Furthermore, in the present invention, the ring n in formula (1) is not limited as long as it has HDAC inhibition activity and, for example, n is preferably 4 to 7, more preferably 5. The carbon chain comprising n carbon atoms, from the cyclic tetrapeptide structure to the sulfur atom, is supposed to enter the active HDAC pocket, and inhibit HDAC by contacting the active thiol group at the carbon chain end with the zinc molecule in the HDAC pocket.

Typical examples of the compounds of the present invention are shown in FIGS. 1 to 3, but are not limited to these compounds.

Hereinafter, methods of producing the compounds of the present invention will be described. The compounds of this embodiment can be produced from 2-amino-n-haloalkanoic acid, as shown below. Since $R_{11}$, $R_{21}$, $R_{22}$, $R_{23}$, $R_{31}$, $R_{32}$, $R_{33}$, $R_{41}$, $R_{42}$, $R_{43}$, and n are defined according to the above descriptions, their descriptions are omitted.

The first embodiment of methods of production for the compounds of the present invention is a method that uses as raw material a compound of formula (2), in which protection group $P_1$ is linked to the amino group of 2-amino-n-haloalkanoic acid. Specifically, a compound defined by the following formula (2)

is reacted with a compound defined by the following formula (3)

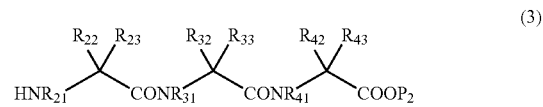

in the presence of a peptide-bonding agent to obtain a compound defined by the following formula (4).

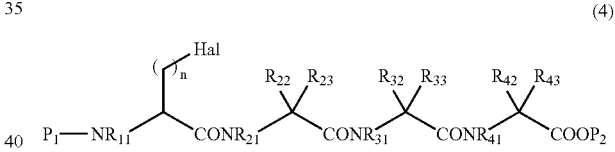

In the above-described formulae, Hal can be a halogen atom selected from any one of a chlorine atom, a bromine atom, or an iodine atom, or an allyl or alkylsulfoxy group that can also be a leaving group. $P_2$ is a protection group for an amino group.

Next, the compound defined by the above-mentioned formula (4) is subjected to catalytic hydrogenation, acid treatment, or hydrolysis for removing $P_1$ and $P_2$, and then to cyclization in the presence of a peptide-bonding agent, to obtain a compound defined by formula (5):

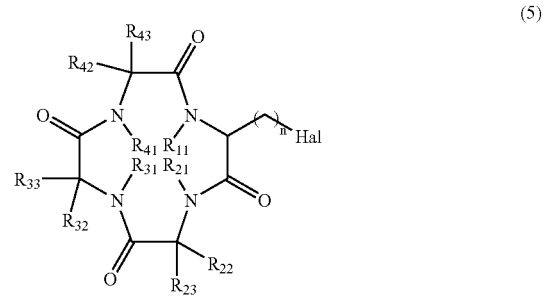

Next, the compound defined by formula (5) is reacted with a reagent comprising a sulfur atom to obtain a compound defined by formula (9):

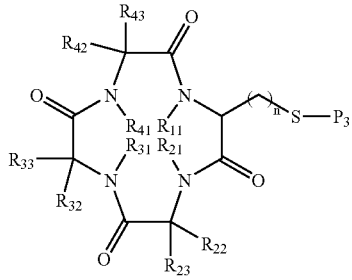

The compound defined by formula (9) is then treated with an oxidizing agent as well as ammonia or another amine to obtain a (dimer- or hybrid-type) prodrug compound comprising a disulfide bond. In formula (9), $P_3$ denotes a protection group for the sulfohydryl group. Treatment with a reducing agent or an enzyme capable of digesting disulfide bonds may be carried out to isolate active thiol-type compounds.

The second embodiment of the production methods of the present invention is a production method that uses as raw material a compound defined by the following formula (7), in which a protection group $P_2$ is linked to the carboxyl group of 2-amino-n-haloalkanoic acid. Specifically, a compound defined by formula (6)

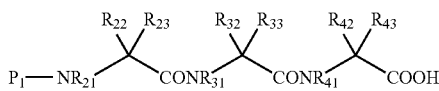

is reacted with a compound defined by formula (7)

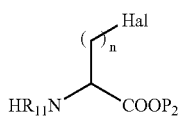

in the presence of peptide-bonding agent, to obtain a compound defined by the following formula (8):

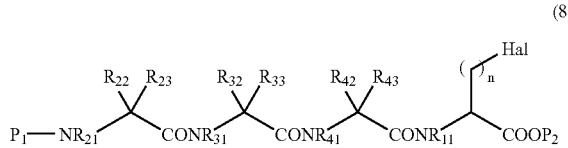

The compound defined by formula (8) is then subjected to catalytic hydrogenation, acid treatment, fluoride anion treatment, or hydrolysis to remove $P_1$ and $P_2$, and then subjected to cyclization in the presence of a peptide-bonding agent, to obtain a compound defined by formula (5). Next, the compound defined by formula (5) is reacted with a sulfur-atom-comprising reagent to obtain a compound defined by formula (9):

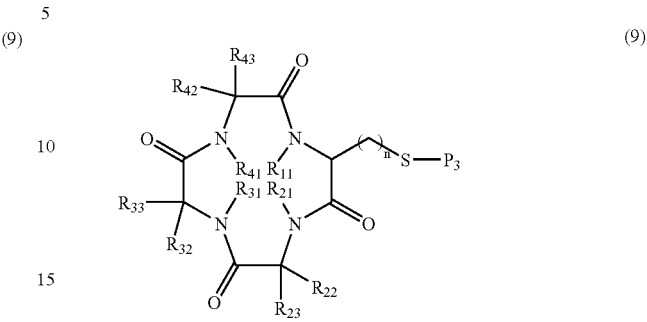

The compound defined by formula (9) is then treated with an oxidizing agent as well as ammonia or another amine to obtain a (dimer- or hybrid-type) prodrug compound comprising a disulfide bond. As for the above-mentioned first embodiment, active thiol-type compounds may be isolated by treatment with a reducing agent or an enzyme capable of digesting disulfide bonds.

HDAC-inhibiting compounds are known to induce differentiation of cancer cells, leukemia cells, and neural cells, to induce apoptosis, and suppress cancer cell metastasis (Yoshida, M., Nomura, S., and Beppu, T. Effects of trichostatins on differentiation of murine erythroleukemia cells. Cancer Res. 47: 3688-3691, 1987; Hoshikawa, Y., Kijima, M., Yoshida, M., and Beppu, T. Expression of differentiation-related markers in teratocarcinoma cells via histone hyper-acetylation by trichostatin A. Agric. Biol. Chem. 55: 1491-1495, 1991; Minucci, S., Horn, V., Bhattacharyya, N., Russanova, V., Ogryzko, V. V., Gabriele, L., Howard, B. H., and Ozato, K. A histone deacetylase inhibitor potentiates retinoid receptor action in embryonal carcinoma cells. Proc. Natl. Acad. Sci. USA 94: 11295-11300, 1997; Inokoshi, J., Katagiri, M., Arima, S., Tanaka, H., Hayashi, M., Kim, Y. B., Furumai, R., Yoshida, M., Horinouchi, S., and Omura, S. (1999). Neuronal differentiation of Neuro 2a cells by inhibitors of cell progression, trichostatin A and butyrolactone I. Biochem. Biophys. Res. Commun. 256, 372-376; Wang, J., Saunthararajah, Y., Redner, R. L., and Liu, J. M. Inhibitors of histone deacetylase relieve ETO-mediated repression and induce differentiation of AML1-ETO leukemia cells. Cancer Res. 59: 2766-2769, 1999; Munster, P. N., Troso-Sandoval, T., Rosen, N., Rifkind, R., Marks, P. A., and Richon, V. M. The histone deacetylase inhibitor suberoylanilide hydroxamic acid induces differentiation of human breast cancer cells. Cancer Res. 61: 8492-8497, 2001; Ferrara, F. F., Fazi, F., Bianchini, A., Padula, F., Gelmetti, V., Minucci, S., Mancini, M., Pelicci, P. G., Lo Coco, F., and Nervi, C. Histone deacetylase-targeted treatment restores retinoic acid signaling and differentiation in acute myeloid leukemia. Cancer Res. 61: 2-7, 2001; Gottlicher, M., Minucci, S., Zhu, P., Kramer, O. H., Schimpf, A., Giavara, S., Sleeman, J. P., Lo Coco, F., Nervi, C., Pelicci, P. G., and Heinzel, T. Valproic acid defines a novel class of HDAC inhibitors inducing differentiation of transformed cells. EMBO J. 20: 6969-6978, 2001). Accordingly, the compounds of the present invention can be utilized as apoptosis-inducing agents, differentiation-inducing agents, and cancer-metastasis-suppressing agents.

Also, the compounds inhibiting HDAC are expected to inhibit angiogenesis (Kim, M. S., Kwon, H. J., Lee, Y. M., Baek, J. H., Jang, J. E., Lee, S. W., Moon, E. J., Kim, H. S., Lee, S. K., Chung, H. Y., Kim, C. W., and Kim, K. W. (2001). Histone deacetylases induce angiogenesis by negative regulation of tumor suppressor genes. Nature Med. 7, 437-443; Kwon, H. J., Kim, M. S., Kim, M. J., Nakajima, H., and Kim, K. W. (2002). Histone deacetylase inhibitor FK228 inhibits tumor angiogenesis. Int. J. Cancer 97, 290-296). Thus, the compounds of the present invention can be also utilized as angiogenesis inhibitors.

Among various HDACs, the compounds of the present invention exhibit a strong inhibitive activity specific to HDAC1 and HDAC4. Therefore, the compounds of the present invention are useful as pharmaceutical agents for treating or preventing diseases caused by HDAC1 and HDAC4. Examples of such diseases besides cancer include autoimmune diseases, skin diseases, and infectious diseases associated with HDAC1 and HDAC4. Furthermore, the compounds of the present invention may be applied not only to pharmaceutical agents for treating or preventing the above-mentioned diseases, but also to gene therapy adjuvants or accelerating agents that improve the efficiency of vector introduction, promote the expression of introduced genes, and the like.

The compounds of the present invention may also be used in combination with retinoic acids and DNA methylation inhibitors. The invention also provides such concomitant agents.

When formulating the compounds of the present invention, fillers, extenders, binders, moisturizing agents, disintegrators, surfactants, diluents such as lubricants, and vehicles may be used as necessary. Furthermore, coloring agents, preservatives, aromatics, flavors, sweeteners, and other pharmaceuticals may be added to the pharmaceutical formulations. The form of each type of pharmaceutical formulation may be selected in line with its therapeutic or preventative purpose. The form may be, for example, a tablet, pill, powder, solution, suspension, emulsion, granule, capsule, injection, and suppository.

Examples of additives to be added to tablets and capsules include binders such as gelatin, corn starch, tragacanth gum, and acacia; vehicles such as crystalline cellulose; swelling agents such as corn starch, gelatin, and alginic acid; lubricants such as magnesium stearate; sweeteners such as sucrose, lactose, and saccharine; and aromatics such as peppermint, Gaultheria adenothrix oil, and cherry. In the case where the unit dosage form is a capsule, a liquid carrier such as oil or fat can be added in addition to the above-mentioned materials.

As an aqueous solution for injection, an isotonic solution of, for example, D-sorbitol, D-mannose, D-mannitol, or sodium chloride comprising saline, glucose, and other adjuvants may also be used as necessary in combination with a proper dissolution-assisting agent, such as an alcohol, specifically, ethanol, a polyalcohol such as propylene glycol and polyethylene glycol, or a nonionic surfactant such as polysorbate 80™ and HCO-50.

Examples of an oleaginous solution are sesame oil and soybean oil, which can be used, as necessary, in combination with a dissolution-assisting agent such as benzyl benzoate and benzyl alcohol. Furthermore, mixing with a buffer such as phosphate buffer solution or sodium acetate buffer solution; a soothing agent such as procaine hydrochloride; a stabilizer such as benzyl alcohol and phenol; or an antioxidant is also acceptable. The formulated injection is generally filled into suitable ampules.

Formulations may be administered to patients orally or parenterally. Examples of a parenteral dosage form, include injection as well as transnasal, transpulmonal, and transdermal administration. Systemic or local administration can be carried out using an injection dosage form, such as intravenous injection, intramuscular injection, intraperitoneal injection, and subcutaneous injection. Furthermore, intranasal, transbronchial, intramuscular, subcutaneous, or oral administration may also be carried out by methods known to those skilled in the art.

For parenteral administration, the unit dosage of the compounds of the present invention depends on the subjects to be administrated, the target organs, symptoms, and the manner of administration. For example, it is preferable that injections are administered intravenously to adults (60 kg body weight) at a dosage of about 0.01 to 30 mg per day, preferably about 0.1 to 20 mg per day, and more preferably about 0.1 to 10 mg per day. When administering to other kind of animals, dosage can be converted per 60 kg body weight, or per unit of body surface area.

For oral administration, the unit dosage of the compounds of the present invention depends on the subjects to be administrated, the target organs, symptoms, and manner of administration, and is preferably, for example, about 100 μg to 20 mg per day for an adult (60 kg body weight).

BRIEF DESCRIPTIONS OF THE DRAWINGS

BEST MODE FOR CARRYING OUT THE INVENTION

Figure 1:
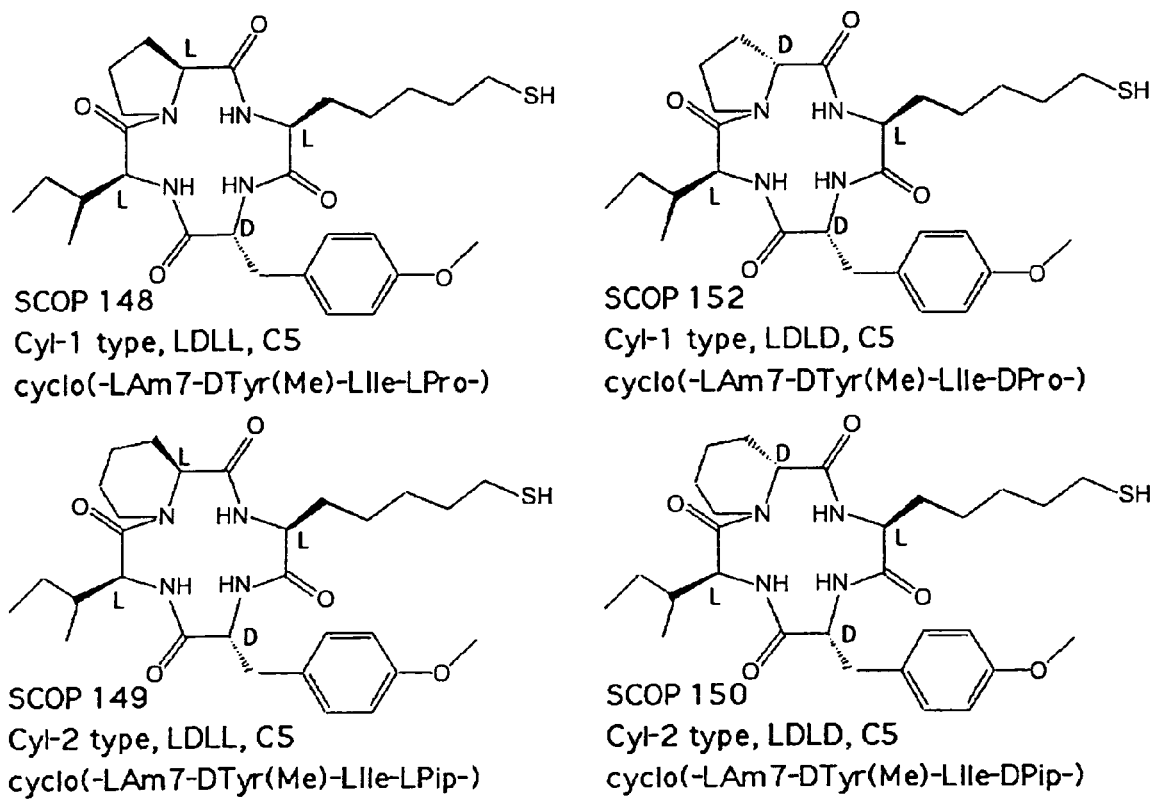
FIG. 1 shows a list of the structure of LDLD or LDLL isomers of SCOP with five carbon chains until the active thiol group.
Figure 2:
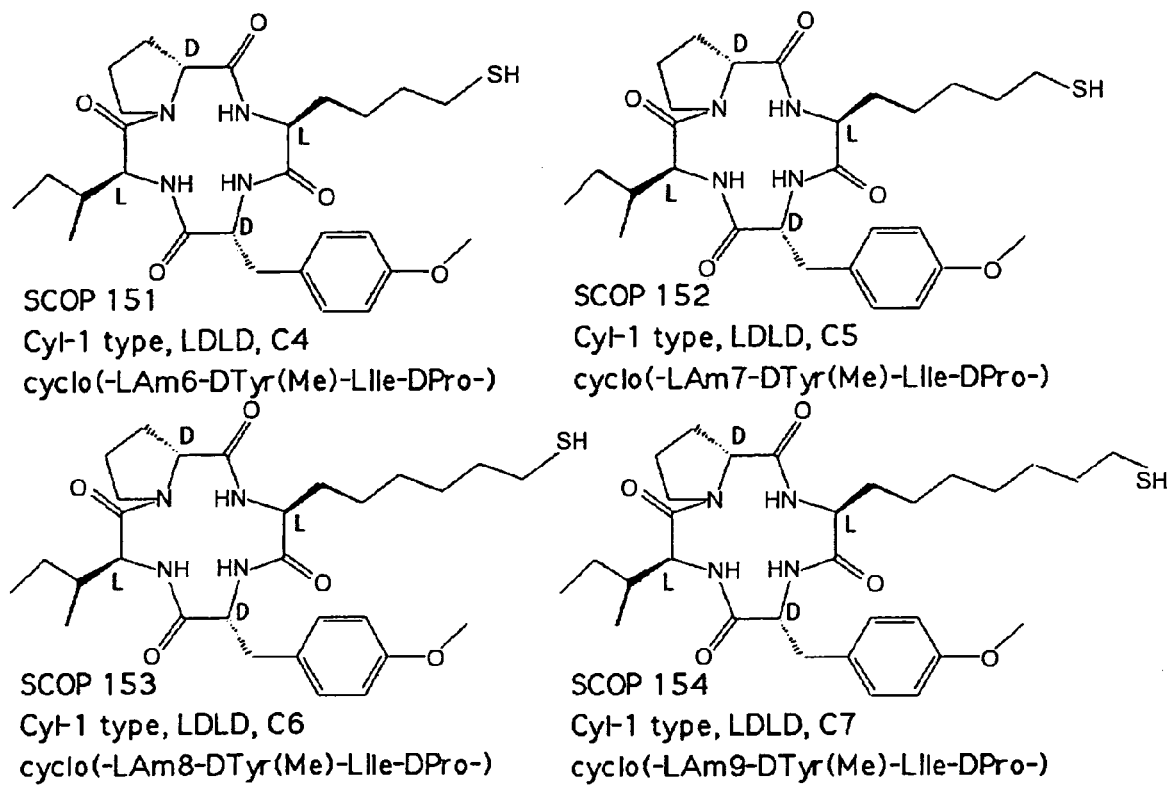
FIG. 2 shows the structures of SCOPs with four to seven carbon chains until the active thiol group. Note that SCOP 152 (C5) is the same here as in FIG. 1.
Figure 3:
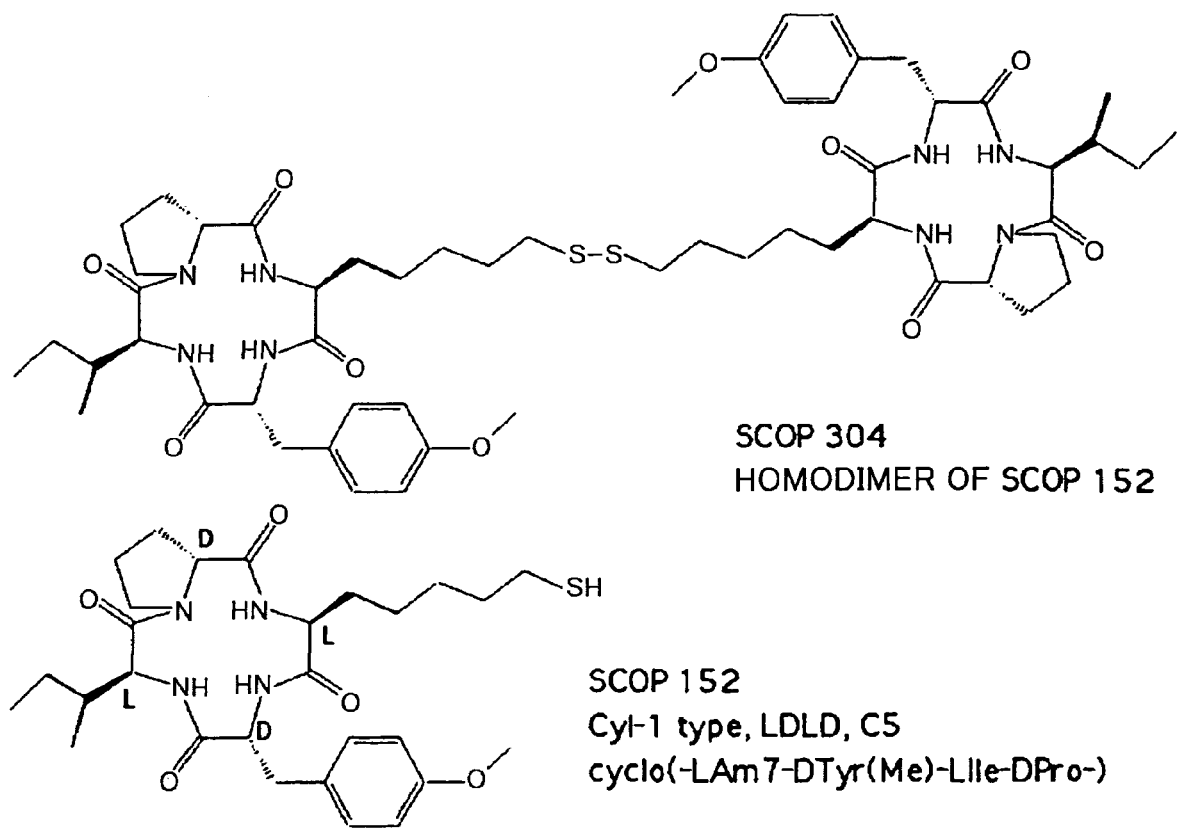
FIG. 3 shows the structures of homodimer-type SCOPs. The SCOP numbers are twice the number of monomers.
Figure 4:
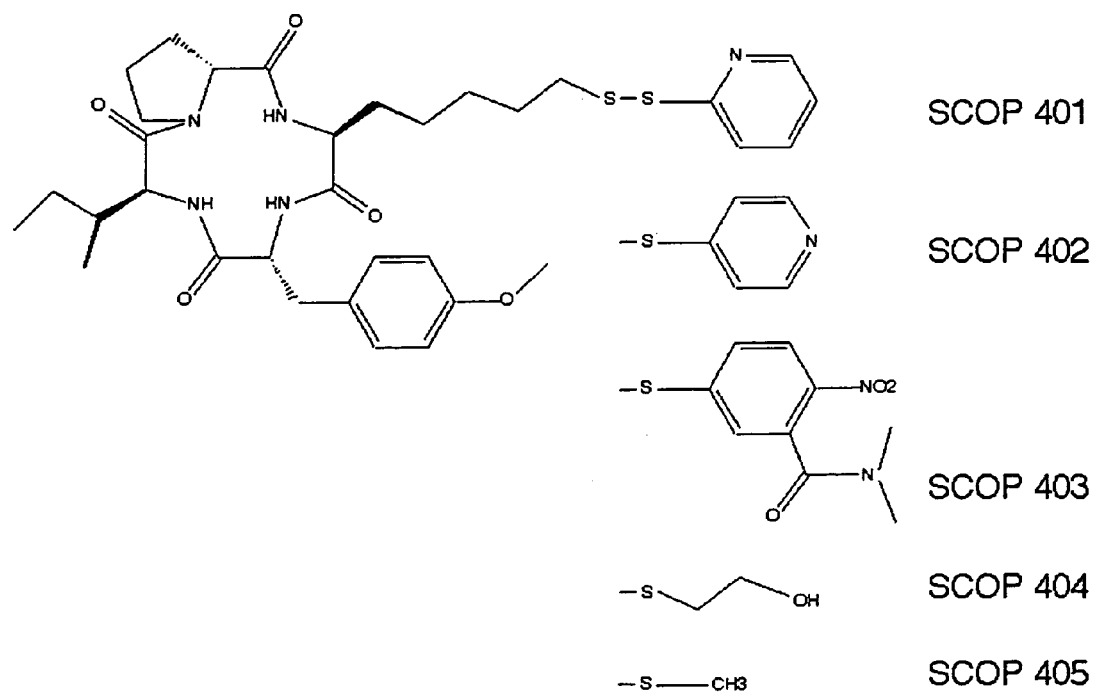
FIG. 4 shows the structures of hybrid-type SCOPs, obtained by bonding a variety of compounds to SCOP 152.

Hereinafter, FIGS. 1 and 2 show the entire flow of the process of synthesizing the compounds shown in these examples. Each synthesis step is described in detail below, with H-L-Ab7-OH as the starting material. In the following, 2-amino-7-bromoheptanoic acid is abbreviated to "Ab7"; 2-amino-7-acetyltioheptanoic acid is "Am7(Ac)"; 2-amino-7-mercaptoheptanioc acid is "Am7"; sulfide of 2-amino-7-mercaptoheptanioc acid is "Am7(-)"; 2-amino-8,9-dimercapto($S^9$-2'-nitro-N,N'-dimethyl benzamide) is "Am7(Ell)"; 2-amino-8,9-dimercapto-11-hydroxyundecanoic acid is "Am7(SMEt)"; 2-amino-8,9-dimercapto($S^9$-2'-pyridyl) nonanoic acid is "Am7(S2Py)"; 2-amino-8,9-dimercapto($S^9$-4'-pyridyl) nonanoic acid is "Am7(S4Py)"; and 2-amino-8,9-dimercaptodecanoic acid is "Am7(SMe)". In addition, sulfur-containing cyclic peptides, which are synthesized compounds, are abbreviated to "SCOP".

EXAMPLE 1

Synthesis of Boc-L-Ab7-OH

H-L-Ab7-OH (7.3 g, 32.4 mmol) was dissolved in water:dioxane=1:1 solution (30 ml, v/v). While cooling on ice, $(Boc)_2O$ (7.68 g, 35.6 mmol) and triethylamine (6.72 ml, 48.6 mmol) were added to the mixture, which was then stirred for five hours. After the reaction solution was evaporated, the residue was washed with ether. The aqueous phase was acidified using citric acid and reverse-extracted with ethyl acetate. The extract was dried over $MgSO_4$ and ethyl acetate was then removed by evaporation. After vacuum drying, the oily title compound (10.4 g, 32.4 mmol, 100% yield) was obtained.

EXAMPLE 2

Synthesis of Boc-L-Ab7-NHMe

While cooling on ice, triethylamine (0.17 ml, 1.2 mmol) and DCC (247 mg, 1.2 mmol) were added to 3 ml of DMF containing Boc-L-Ab7-OH (326 mg, 1.0 mmol), monomethylamine hydrochloride (81 mg, 1.2 mmol), and $HOBt.H_2O$ (184 mg, 1.2 mmol). After stirring for 15 hours, the DMF was removed by evaporation. The residue was dissolved in ethyl acetate and successively washed with an aqueous 10% citric acid solution, an aqueous 4% sodium bicarbonate solution, and saturated saline. This was then dried over $MgSO_4$ and concentrated. The resulting oily substance was purified by flash silica gel chromatography (3.6×15 cm, chloroform) and solidified by adding ether/petroleum ether (1:10) to obtain the white powder of the title compound (250 mg, 0.74 mmol, 74% yield). TLC: Rf=0.58 ($CHCl_3$/MeOH=9/1).

EXAMPLE 3

Synthesis of Boc-L-Am7(Ac)-NHMe

Potassium thioacetate (64 mg, 0.56 mmol) was added to DMF (2 ml) containing Boc-Ab7-NHMe (125 mg, 0.37 mmol) and reacted for 3 hours. After DMF was removed by evaporation, the residue was dissolved in ethyl acetate and successively washed with an aqueous 10% citric acid solution and saturated saline. The product was dried over $MgSO_4$, concentrated, and solidified by adding ether/petroleum ether (1:10) to obtain the white powder of the title compound (120 mg, 0.36 mmol, 97% yield). TLC: Rf=0.57 ($CHCl_3$/MeOH=9/1).

EXAMPLE 4

Synthesis of Boc-L-Am7(-)-NHMe SS-dimer

Methanolic ammonia (20 eq.) was added to DMF (0.5 ml) containing Boc-Am7(Ac)-NHMe (60 mg, 0.18 mmol) and stirred for 24 hours. After concentrating the reaction solution, the SS-dimer produced was purified by flash silica gel chromatography (1.5×30 cm, 1% methanol/chloroform) to obtain the white powder of the title compound (43 mg, 0.11 mmol, 61% yield). HPLC retention time: 8.5 min; HRMS (FAB, dithiodiethanol), 579.3293 [M+H], $C_{26}H_{51}O_6N_4S_2$ (579.3250).

EXAMPLE 5

Synthesis of Boc-L-Am7(S4Py)-NHMe 4,4'-dithiodipyridine (79 mg, 0.36 mmol) and methanolic ammonia (20 eq.) were added to DMF (0.5 ml) containing Boc-Am7(Ac)-NHMe (60 mg, 0.18 mmol), and stirred for 5 hours. After the reaction solution was concentrated, the resulting oily product was purified by flash silica gel chromatography (1.5×30 cm, chloroform) and freeze-dried to obtain the title compound (43 mg, 0.11 mmol, 61% yield). HPLC retention time: 5.6 min; HRMS (FAB, dithiodiethanol), 400.1766 [M+H], $C_{18}H_{29}O_3N_3S_2$ (400.1729).

EXAMPLE 6

Synthesis of Boc-L-Ab7-OBzl

Boc-L-Ab7-OH (4.05 g, 12.5 mmol) was dissolved in DCM (20 ml). While cooling on ice, benzyl alcohol (1.55 ml, 15.0 mmol), 4-dimethylaminopyridine (153 mg, 1.25 mmol), and DCC (3.09 g, 15.0 mmol) were added to the mixture, which was then stirred for 8 hours. After the reaction solution was evaporated, the residue was dissolved in ethyl acetate and successively washed with an aqueous 10% citric acid solution, an aqueous 4% sodium bicarbonate solution, and saturated saline. This was then dried over $MgSO_4$, concentrated, and the resulting oily substance was purified by flash silica gel chromatography (5×20 cm, 20% ethyl acetate/hexane) to obtain the oily title compound (4.29 g, 10.4 mmol, 83% yield). TLC: Rf=0.49 (ethyl acetate/hexane=1/4).

EXAMPLE 7

Synthesis of Boc-L-Ile-L-Pro-OBzl

While cooling on ice, Boc-L-Pro-OH (1.08 g, 5.0 mmol) and benzyl bromide (0.893 ml, 75 mmol) were reacted in DMF (10 ml) in the presence of triethylamine (10.5 ml, 75 mmol) to obtain Boc-L-Pro-OBzl as an oily product. This product was reacted under ice-cooling with 2 N HCl/dioxane (5 eq.) for three hours to obtain H-L-Pro-OBzl-HCl.

While cooling on ice, DCC (1.24 g, 6.0 mmol) and triethylamine (0.70 ml, 4.0 mmol) were added to DMF (10 ml) containing Boc-L-Ile-OH.1/2 $H_2O$ (1.39 g, 6.0 mmol), H-D-Pro-OBzl-HCl (956 mg, 4.0 mmol), and $HOBt.H_2O$ (613 mg, 4.0 mmol). After stirring for 8 hours, DMF was removed by evaporation, the residue was dissolved in ethyl acetate, and then successively washed with an aqueous 10% citric acid solution, an aqueous 4% sodium bicarbonate solution, and saturated saline. After drying over $MgSO_4$ and concentrating, the resulting oily substance was purified by flash silica gel chromatography (4×30 cm, 1% methanol/chloroform). to obtain the oily title compound (1.63 g, 3.38 mmol, 85% yield). TLC: Rf=($CHCl_3$/MeOH=9/1)

EXAMPLE 8

Synthesis of Boc-D-Tyr(Me)-L-Ile-L-Pro-OBzl

Boc-L-Ile-L-Pro-OBzl (1.63 g, 3.38 mmol) was dissolved in TFA (5 ml) and left with standing on ice for 30 minutes. On completion of the reaction, TFA was removed by evaporation, and the residue was vacuum-dried to obtain H-L-Ile-L-Pro-OBzl-TFA. The compound was dissolved in DMF (8 ml), and Boc-D-Tyr(Me)-OH (1.50 g, 5.07 mmol) was then added. HBTU (1.92 g, 5.07 mmol), $HOBt.H_2O$ (518 mg, 3.38 mmol), and triethylamine (2.37 ml, 16.9 mmol) were further added and stirred for three hours under ice-cooling. The reaction solution was concentrated, dissolved in ethyl acetate, and successively washed with an aqueous 10% citric acid solution, an aqueous 4% sodium bicarbonate solution, and saturated saline. The product was dried over $MgSO_4$ and concentrated, and the resulting foam substance was purified by flash silica gel chromatography (4×30 cm, 1% methanol/chloroform) to obtain the foam title compound (1.44 g, 2.42 mmol, 72% yield). TLC: Rf=(CHCl$_3$/MeOH=9/1).

EXAMPLE 9

Synthesis of Boc-D-Tyr(Me)-L-Ile-L-Pro-L-Ab7-OBzl

Boc-D-Tyr(Me)-L-Ile-L-Pro-OBzl (1.44 g, 2.42 mmol) was dissolved in methanol (12 ml) and subjected to catalytic hydrogenation in the presence of the 5% Pd-C (150 mg). After five hours, the catalyst Pd-C was filtered and the reaction solution was removed by evaporation to obtain Boc-D-Tyr (Me)-L-Ile-L-Pro-OH-TFA.

Boc-L-Ab7-OBzl (1.29 g, 3.12 mmol) was dissolved in TFA (10 ml) and left with standing on ice for 30 minutes. On completion of the reaction, TFA was removed by evaporation, and the residue was vacuum-dried to obtain H-L-Ab7-OH-TFA. The compound was dissolved in DMF (16 ml), and Boc-D-Tyr(Me)-L-Ile-L-Pro-OH (1.21 g, 2.40 mmol) was then added. HBTU (1.18 g, 3.12 mmol), HOBt.H$_2$O (368 mg, 2.40 mmol), and triethylamine (1.34 ml, 9.6 mmol) were further added and stirred for 3 hours under ice-cooling. The reaction solution was concentrated, dissolved in ethyl acetate, and successively washed with 10% citric acid, an aqueous 4% sodium bicarbonate solution, and saturated saline. The product was dried over MgSO$_4$ and concentrated, and the resulting foam substance was purified by flash silica gel chromatography (4×30 cm, 2% methanol/chloroform) to obtain the foam title compound (1.20 g, 1.47 mmol, 61% yield). TLC: Rf= (CHCl$_3$/MeOH=9/1).

EXAMPLE 10

Synthesis of H-D-Tyr(Me)-L-Ile-L-Pro-L-Ab7-OH.TFA

Boc-D-Tyr(Me)-L-Ile-L-Pro-L-Ab7-OBzl (1.20 g, 1.47 mmol) was dissolved in methanol (7.5 ml) and subjected to catalytic hydrogenation in the presence of the catalyst Pd-C (130 mg). After 5 hours, the catalyst Pd-C was filtered and the reaction solution was removed by evaporation to obtain Boc-D-Tyr(Me)-L-Ile-L-Pro-L-Ab7-OH. This compound was dissolved in TFA (5 ml) and left standing on ice for 30 minutes. After the reaction solution was removed by evaporation, ether/petroleum ether (1:10) was added to the residue for solidification. This was then vacuum-dried to obtain the title compound (770 mg, 1.02 mmol, 69% yield).

EXAMPLE 11

Synthesis of cyclo(-L-Ab7-D-Tyr(Me)-L-Ile-L-Pro-)

H-D-Tyr(Me)-L-Ile-L-Pro-L-Ab7-OH.TFA (770 mg, 1.02 mmol), HATU (388 mg, 1.53 mmol), and DIEA (0.71 ml) were divided into five aliquots. DMF (1000 ml) was added to each aliquot every 30 minutes, and cyclization reaction was carried out. After 2 hours, the solvent was removed by evaporation. The residue was dissolved in ethyl acetate, successively washed with an aqueous 10% citric acid solution, 4% NaHCO$_3$, and saturated saline, and then dried with MgSO$_4$. Ethyl acetate was removed by evaporation, and the remaining oily substance was purified by flash silica gel chromatography (4×30 cm, 2% methanol/chloroform) to obtain a foam substance 130 mg (21%). HPLC retention time: 8.20 min; FAB-MS (dithiodiethanol), 593 [M+H], (593.2).

EXAMPLE 12

Synthesis of cyclo(-L-Am7(Ac)-D-Tyr(Me)-L-Ile-L-Pro-)

Potassium thioacetate (9.59 mg, 0.084 mmol) was added to DMF (0.5 ml) containing cyclo(-L-Ab7-D-Tyr(Me)-L-Ile-L-Pro-) (25 mg, 0.042 mmol) and reacted for 3 hours. DMF was removed by evaporation. The residue was dissolved in ethyl acetate and then successively washed with aqueous 10% citric acid solution, 4% NaHCO$_3$, and saturated saline. The thioester produced similarly after the cyclization reaction was isolated and purified to obtain 19 mg (76%) of oily product. HPLC retention time: 8.20 min; FAB-MS (dithiodiethanol), 589 [M+H], (589.3).

EXAMPLE 13

Synthesis of cyclo(-L-Am7(-)-D-Tyr(Me)-L-Ile-L-Pro-) (SS-dimer: SCOP 296)

Cyclo(-L-Am7(Ac)-D-Tyr(Me)-L-Ile-L-Pro-) (19 mg, 0.0322 mmol) was dissolved in hot DMF (2 ml) and reacted with methanolic ammonia (10 eq.) to remove the acetyl groups. After the solvent was removed by evaporation, the residue was dissolved in DMF (2 ml), and 1 M I$_2$ (ethanol) (0.04 ml) was added to the solution for oxidization. The produced SS-dimer was purified through a Sephadex LH-20 (DMF) column and then mixed with water to obtain a white powder. The yield was 7.4 mg (42%). HPLC retention time: 14.1 min; HRMS (FAB, dithiodiethanol), 1091.5648 [M+H], C$_{56}$H$_{83}$O$_{10}$N$_8$S$_2$ (1091.5674).

EXAMPLE 14

Synthesis of Boc-L-Ile-DL-Pip-OBzl

Boc-DL-Pip-OH (2.29 g, 10 mmol) and benzyl bromide (1.79 ml, 15 mmol) were reacted in DMF (20 ml) in the presence of triethylamine (2.1 ml, 15 mmol) to obtain Boc-DL-Pip-OBzl as an oily product. This product was reacted with 2 N HCl/dioxane (5 eq.) for 3 hours to obtain H-DL-Pip-OBzl-HCl.

While cooling on ice, DCC (2.20 g, 10.7 mmol) and triethylamine (1.25 ml, 8.9 mmol) were added to DMF (20 ml) containing Boc-L-Ile-OH.1/2 H$_2$O (2.47 g, 10.7 mmol), H-D-Pro-OBzl-HCl (2.28 g, 8.9 mmol), and HOBt.H$_2$O (1.36 mg, 8.9 mmol). After stirring for 8 hours, DMF was removed by evaporation, the residue was dissolved in ethyl acetate, and then successively washed with an aqueous 10% citric acid solution, an aqueous 4% sodium bicarbonate solution, and saturated saline. After drying over MgSO$_4$ and concentrating, the resulting oily substance was purified by flash silica gel chromatography (4×30 cm, 1% methanol/chloroform) to obtain the oily title diastereomer mixture (3.33 g, 7.70 mmol, 87% yield). TLC: Rf=(CHCl$_3$/MeOH=9/1)

EXAMPLE 15

Synthesis of Boc-D-Tyr(Me)-L-Ile-DL-Pip-OBzl

Boc-L-Ile-DL-Pip-OBzl (3.33 g, 7.70 mmol) was dissolved in TFA (10 ml) and left with standing on ice for 30 minutes. On completion of the reaction, TFA was removed by evaporation, and the residue was vacuum-dried to obtain H-L-Ile-DL-Pip-OBzl.TFA. The compound was dissolved in DMF (16 ml), and Boc-D-Tyr(Me)-OH (3.41 g, 11.6 mmol) was then added. HBTU (4.38 g, 11.6 mmol), HOBt.H$_2$O (1.18 g, 7.70 mmol), and triethylamine (7.01 ml, 50.1 mmol) were further added and stirred for 3 hours under ice-cooling. The reaction solution was concentrated, dissolved in ethyl acetate, and successively washed with an aqueous 10% citric acid solution, an aqueous 4% sodium bicarbonate solution, and saturated saline. The product was dried over MgSO$_4$ and concentrated, and the resulting foam substance was purified by flash silica gel chromatography (4×30 cm, 1% methanol/chloroform) to obtain the foam title diastereomer mixture (3.46 g, 5.67 mmol, 74% yield). TLC: Rf=(CHCl$_3$/MeOH=9/1).

EXAMPLE 16

Synthesis of Boc-D-Tyr(Me)-L-Ile-DL-Pip-L-Ab7-OBzl

Boc-D-Tyr(Me)-L-Ile-DL-Pip-OBzl (3.46 g, 7.37 mmol) was dissolved in methanol (30 ml) and subjected to catalytic hydrogenation in the presence of the 5% Pd-C (230 mg). After 8 hours, the catalyst Pd-C was filtered and the reaction solution was evaporated to obtain Boc-D-Tyr(Me)-L-Ile-DL-Pip-OH.

Boc-L-Ab7-OBzl (3.05 g, 3.12 mmol) was dissolved in TFA (5 ml) and left with standing on ice for 30 minutes. On completion of the reaction, TFA was removed by evaporation, and the residue was vacuum-dried to obtain H-L-Ab7-OBzl.TFA. The compound was dissolved in DMF (16 ml), and Boc-D-Tyr(Me)-L-Ile-DL-Pip-OH (2.80 g, 5.39 mmol) was then added. HBTU (2.66 g, 7.01 mmol), HOBt.H$_2$O (825 mg, 5.39 mmol), and triethylamine (3.02 ml, 21.6 mmol) were further added and stirred for 3 hours under ice-cooling. The reaction solution was concentrated, dissolved in ethyl acetate, and successively washed with an aqueous 10% citric acid solution, an aqueous 4% sodium bicarbonate solution, and saturated saline. The product was dried over MgSO$_4$ and concentrated, and the resulting foam substance was purified by flash silica gel chromatography (4×30 cm, 2% methanol/chloroform) to obtain the foam title diastereomer mixture (4.07 g, 4.91 mmol, 91% yield). TLC: Rf=(CHCl$_3$/MeOH=9/1).

EXAMPLE 17

Synthesis of H-D-Tyr(Me)-L-Ile-DL-Pip-L-Ab7-OH.TFA

Boc-D-Tyr(Me)-L-Ile-L-Pro-DL-Pip-OBzl (4.07 g, 4.91 mmol) was dissolved in methanol (10 ml) and subjected to catalytic hydrogenation in the presence of the catalyst Pd-C (300 mg). After 8 hours, the catalyst Pd-C was filtered and the reaction solution was removed by evaporation to obtain Boc-D-Tyr(Me)-L-Ile-DL-Pip-OH. This compound was dissolved in TFA (10 ml) and left standing on ice for 30 minutes. After the reaction solution was concentrated by evaporation, ether/petroleum ether (1:10) was added to the residue for solidification. This was then vacuum-dried to obtain the title diastereomer mixture (2.60 g, 3.51 mmol, 72% yield).

EXAMPLE 18

Synthesis of cyclo(-L-Ab7-D-Tyr(Me)-L-Ile-L-Pip-) and cyclo(-L-Ab7-D-Tyr(Me)-L-Ile-D-Pip-)

A linear tetrapeptide, H-D-Tyr(Me)-L-Ile-DL-Pip-L-Ab7-OH (1.28 g, 2.0 mmol), HATU (1.14 g, 3.0 mmol), and DIEA (1.0 ml) were divided into five aliquots. DMF (1000 ml) was added to each aliquot every 30 minutes, and cyclization reaction was carried out. After 2 hours, the reaction solution was concentrated, dissolved in ethyl acetate, and successively washed with an aqueous 10% citric acid solution, an aqueous 4% sodium bicarbonate solution, and saturated saline. After drying up over MgSO$_4$ and concentrating, the resulting foam substance was purified by flash silica gel chromatography (4×30 cm, 2% methanol/chloroform) to obtain a foam cyclo (-L-Ab7-D-Tyr(Me)-L-Ile-L-Pip-) (372 mg, 61%; HPLC retention time: 8.94 min; FAB-MS (dithiodiethanol), 607 [M+H], (607.2)) and a foam cyclo(-L-Am7(-)-D-Tyr(Me)-L-Ile-D-Pip-) (238 mg, 39%; HPLC retention time: 10.5 min; FAB-MS (dithiodiethanol), 607 [M+H], (607.2)).

EXAMPLE 19

Synthesis of cyclo(-L-Am7(Ac)-D-Tyr(Me)-L-Ile-L-Pip-)

Potassium thioacetate (69 mg, 0.315 mmol) was added to DMF (1 ml) containing cyclo(-L-Ab7-D-Tyr(Me)-L-Ile-L-Pip-) (130 mg, 0.21 mmol) and reacted for 3 hours. The reaction solution was concentrated by evaporation, dissolved in ethyl acetate, and then successively washed with aqueous 10% citric acid solution and saturated saline. The thioester produced similarly after the cyclization reaction was isolated and purified to obtain 109 mg (86%) of oily product. HPLC retention time: 8.94 min; FAB-MS (dithiodiethanol), 603 [M+H], (603.3).

EXAMPLE 20

Synthesis of cyclo(-L-Am7(-)-D-Tyr(Me)-L-Ile-L-Pip-(SS-dimer: SCOP 298)

Methanol solution (0.5 ml) containing cyclo(-L-Am7(Ac)-D-Tyr(Me)-L-Ile-L-Pip-) (114 mg, 0.198 mmol) was reacted with methanolic ammonia (10 eq.) to remove the acetyl groups. After the solvent was removed by evaporation, the residue was dissolved in DMF (2 ml), and 1 M I$_2$ (ethanol) (0.25 ml) was added to the solution for oxidization. The produced SS-dimer was purified through a Sephadex LH-20 (DMF) column and then mixed with water to obtain a white powder. The yield was 82 mg (78%). HPLC retention time: 11.6 min; HRMS (FAB, dithiodiethanol), 1063.5391 [M+H], $C_{54}H_{79}O_{10}N_8S_2$ (1063.5361).

EXAMPLE 21

Synthesis of cyclo(-L-Am7(Ac)-D-Tyr(Me)-L-Ile-D-Pip-)

Potassium thioacetate (69 mg, 0.60 mmol) was added to DMF (0.5 ml) containing cyclo(-L-Ab7-D-Tyr(Me)-L-Ile-D-Pip-) (240 mg, 0.40 mmol), and this was reacted for 3 hours. The reaction solution was concentrated, dissolved in ethyl acetate, and successively washed with aqueous 10% citric acid solution, an aqueous 4% sodium bicarbonate solution, and saturated saline. After drying over MgSO$_4$ and concentrating, the resulting thioester was isolated and purified in the same manner as after the cyclization reaction to obtain an oily substance (160 mg) (66%). HPLC retention time: 10.5 min; FAB-MS (dithiodiethanol), 603 [M+H], (603.3).

EXAMPLE 22

Synthesis of cyclo(-L-Am7(-)-D-Tyr(Me)-L-Ile-D-Pip-(SS-dimer: SCOP 300)

DMF (10 ml) containing cyclo(-L-Am7(Ac)-D-Tyr(Me)-L-Ile-D-Pip-) (160 mg, 0.27 mmol) was reacted with methanolic ammonia (10 eq.) to remove the acetyl groups. After the solvent was removed by evaporation, the residue was dissolved in DMF (2 ml), and 1 M $I_2$ (ethanol) (0.31 ml) was added to the solution for oxidization. The produced SS-dimer was purified through a Sephadex LH-20 (DMF) column and then mixed with water to obtain a white powder. The yield was 54 mg (36%). HPLC retention time: 13.4 min; HRMS (FAB, dithiodiethanol), 1119.5939 [M+H]⁻, $C_{58}H_{87}O_{10}N_8S_2$ (1119.5986).

EXAMPLE 23

Synthesis of Boc-L-Ile-D-Pro-OBzl

While cooling on ice, Boc-D-Pro-OH (17.2 g, 80 mmol) and benzyl bromide (14.3 ml, 120 mmol) were reacted in DMF (160 ml) in the presence of triethylamine (16.8 ml, 120 mmol) to obtain Boc-D-Pro-OBzl as an oily product. This product was reacted with 2 N HCl/dioxane (5 eq.) for 3 hours to obtain H-D-Pro-OBzl·HCl.

While cooling on ice, DCC (8.3 g, 30 mmol) and triethylamine (3.5 ml, 25 mmol) were added to DMF (200 ml) containing Boc-L-Ile-OH.1/2 $H_2O$ (24.0 g, 100 mmol), H-D-Pro-OBzl·HCl (19.3 g, 80 mmol), and HOBt·$H_2O$ (15.3 g, 100 mmol). After stirring for 8 hours, DMF was removed by evaporation, the residue was dissolved in ethyl acetate, and then successively washed with an aqueous 10% citric acid solution, an aqueous 4% sodium bicarbonate solution, and saturated saline. After drying over $MgSO_4$ and concentrating, the resulting oily substance was purified by flash silica gel chromatography (4×30 cm, 1% methanol/chloroform) to obtain the oily title compound (21.5 g, 51 mmol, 72% yield). TLC: Rf=(CHCl₃/MeOH=9/1)

EXAMPLE 24

Synthesis of Boc-D-Tyr(Me)-L-Ile-D-Pro-OBzl

Boc-L-Ile-D-Pro-OBzl (21.5 g, 51.4 mmol) was dissolved in TFA (50 ml) and left with standing on ice for one hour. On completion of the reaction, TFA was removed by evaporation, and the residue was vacuum-dried to obtain H-L-Ile-D-Pro-OBzl·TFA. The compound was dissolved in DMF (100 ml), and Boc-D-Tyr(Me)-OH (16.7 g, 56.5 mmol) was then added. HBTU (29.4 g, 77 mmol), HOBt·H₂O (7.87 g, 51 mmol), and triethylamine (25.2 ml, 180 mmol) were further added and stirred for 3 hours under ice-cooling. The reaction solution was concentrated, dissolved in ethyl acetate, and successively washed with an aqueous 10% citric acid solution, an aqueous 4% sodium bicarbonate solution, and saturated saline. The product was dried over MgSO₄ and concentrated, and the resulting foam substance was purified by flash silica gel chromatography (4×30 cm, 1% methanol/chloroform) to obtain the foam title compound (22.0 g, 37 mmol, 72% yield). TLC: Rf=(CHCl₃/MeOH=9/1).

EXAMPLE 25

Synthesis of Boc-L-Ab6-OTmse

Boc-L-Ab6-OH (620 mg, 2.0 mmol) and trimethylsilylethanol (0.572 ml, 4.0 mmol) were stirred in DCM (6 ml) for 6 hours in the presence of 4-dimethylamino-pyridine (24.4 mg, 0.2 mmol). The reaction solution was concentrated, dissolved in ethyl acetate, and successively washed with aqueous 10% citric acid solution, aqueous 4% sodium bicarbonate solution, and saturated saline. The product was dried over MgSO₄ and concentrated, and the resulting oily substance was purified by flash silica gel chromatography (4×30 cm, 10% ethyl acetate/hexane) to obtain an oily title compound (820 mg, 1.62 mmol, 81% yield). TLC: Rf=0.97 (CHCl₃/MeOH=9/1).

EXAMPLE 26

Synthesis of Boc-D-Tyr(Me)-L-Ile-D-Pro-L-Ab6-OTmse

Boc-D-Tyr(Me)-L-Ile-D-Pro-OBzl (1.01 g, 1.70 mmol) was dissolved in methanol (20 ml) and subjected to catalytic hydrogenation in the presence of 5% Pd-C (150 mg). After 8 hours, the catalyst Pd-C was filtered and the reaction solution was evaporated to obtain Boc-D-Tyr(Me)-L-Ile-D-Pro-OH.

Boc-L-Ab6-OTmse (1.51 g, 3.0 mmol) was dissolved in TFA (5 ml) and left standing on ice for 30 minutes. On completion of the reaction, the reaction solution was evaporated and the residue was vacuum-dried to obtain H-L-Am6-OTmse-TFA. This product was dissolved in DMF (3.5 ml). Under ice-cooling, Boc-D-Tyr(Me)-L-Ile-D-Pro-OH (819 mg, 1.62 mmol), HATU (776 mg, 2.0 mmol), and triethylamine (0.24 ml, 1.7 mmol) were divided into four aliquots and added to the above-described DMF solution, which was then stirred for 3 hours. The reaction solution was concentrated, dissolved in ethyl acetate, and successively washed with aqueous 10% citric acid solution, aqueous 4% sodium bicarbonate solution, and saturated saline. The resulting product was dried over anhydrous MgSO₄ and concentrated to obtain a foam substance, which was then purified by flash silica gel chromatography (4×30 cm, 1% methanol/chloroform) to obtain the title compound (888 mg, 1.09 mmol, 64% yield). TLC: Rf=(CHCl₃/MeOH=9/1).

EXAMPLE 27

Synthesis of Boc-L-Ab7-D-Tyr(Me)-L-Ile-D-Pro-OBzl

Boc-D-Tyr(Me)-L-Ile-D-Pro-OBzl (1.19 g, 2.0 mmol) was dissolved in TFA (5 ml) and left with standing on ice for 30 minutes. On completion of the reaction, TFA was removed by evaporation, and the residue was vacuum-dried to obtain H-D-Tyr(Me)-L-Ile-D-Pro-OBzl-TFA. The compound was dissolved in DMF (4.0 ml), and Boc-L-Ab7-OH (652 mg, 2.0 mmol) was then added. HBTU (1.14 g, 3.0 mmol), HOBt·H₂O (306 mg, 2.0 mmol), and triethylamine (1.4 ml, 10 mmol) were further added and stirred for 3 hours under ice-cooling. The reaction solution was concentrated, dissolved in ethyl acetate, and successively washed with an aqueous 10% citric acid solution, an aqueous 4% sodium bicarbonate solution, and saturated saline. The product was dried over MgSO₄ and concentrated, and the resulting foam substance was purified by flash silica gel chromatography (4×30 cm, 2% methanol/chloroform) to obtain the foam title compound (1.51 g, 1.89 mmol, 94% yield). HPLC retention time: 9.15 min.

EXAMPLE 28

Synthesis of Boc-L-Ab8-D-Tyr(Me)-L-Ile-D-Pro-OBzl

Boc-D-Tyr(Me)-L-Ile-D-Pro-OBzl (1.19 g, 2.0 mmol) was dissolved in TFA (5 ml) and left with standing on ice for 30 minutes. On completion of the reaction, TFA was removed by evaporation, and the residue was vacuum-dried to obtain H-D-Tyr(Me)-L-Ile-D-Pro-OBzl.TFA. The compound was dissolved in DMF (4.0 ml), and Boc-L-Ab8-OH (676 mg, 2.0 mmol) was then added. HBTU (1.14 g, 3.0 mmol), HOBt.$H_2O$ (306 mg, 2.0 mmol), and triethylamine (1.4 ml, 10 mmol) were further added and stirred for 3 hours under ice-cooling. The reaction solution was concentrated, dissolved in ethyl acetate, and successively washed with an aqueous 10% citric acid solution, an aqueous 4% sodium bicarbonate solution, and saturated saline. The product was dried over $MgSO_4$ and concentrated, and the resulting foam substance was purified by flash silica gel chromatography (4×30 cm, 2% methanol/chloroform) to obtain the foam title compound (1.44 g, 1.76 mmol, 88% yield). HPLC retention time: 10.9 min.

EXAMPLE 29

Synthesis of Boc-L-Ab9-D-Tyr(Me)-L-Ile-D-Pro-OBzl

Boc-D-Tyr(Me)-L-Ile-D-Pro-OBzl (1.19 g, 2.0 mmol) was dissolved in TFA (5 ml) and left with standing on ice for 30 minutes. On completion of the reaction, TFA was removed by evaporation, and the residue was vacuum-dried to obtain H-D-Tyr(Me)-L-Ile-D-Pro-OBzl.TFA. The compound was dissolved in DMF (4.0 ml), and Boc-L-Ab9-OH (775 mg, 2.2 mmol) was then added. HBTU (1.14 g, 3.0 mmol), HOBt.$H_2O$ (306 mg, 2.0 mmol), and triethylamine (1.4 ml, 10 mmol) were further added and stirred for 3 hours under ice-cooling. The reaction solution was concentrated, dissolved in ethyl acetate, and successively washed with an aqueous 10% citric acid solution, an aqueous 4% sodium bicarbonate solution, and saturated saline. The product was dried over $MgSO_4$ and concentrated, and the resulting foam substance was purified by flash silica gel chromatography (4×30 cm, 2% methanol/chloroform) to obtain the foam title compound (1.31 g, 1.58 mmol, 79% yield). HPLC retention time: 11.7 min.

EXAMPLE 30

Synthesis of H-D-Tyr(Me)-L-Ile-D-Pro-L-Ab6-OH.TFA

Boc-D-Tyr(Me)-L-Ile-D-Pro-L-Ab6-OTmse (888 mg, 1.11 mmol) was dissolved in ethanol (10 ml). Under ice-cooling, an aqueous 1 N NaOH solution (1.32 ml, 1.33 mmol) divided into three aliquots was added to the solution and left standing on ice for 3 hours. The reaction solution was concentrated, dissolved in ethyl acetate, and successively washed with 10% citric acid and saturated saline. After drying over $MgSO_4$, the product was concentrated to obtain Boc-D-Tyr(Me)-L-Ile-D-Pro-L-Ab6-OH. The compound was dissolved in TFA (5 ml) and left standing on ice for 30 minutes. The reaction solution was evaporated, and the residue was vacuum-dried to obtain an oily title compound (778 mg, 1.07 mmol, 96% yield).

EXAMPLE 31

Synthesis of H-L-Ab7-D-Tyr(Me)-L-Ile-D-Pro-OH.TFA

Boc-L-Ab7-D-Tyr(Me)-L-Ile-D-Pro-OBzl (1.51 g, 1.89 mmol) was dissolved in methanol (5 ml) and subjected to catalytic hydrogenation in the presence of 5% Pd-C (150 mg). After 5 hours, the catalyst Pd-C was filtered and the reaction solution was evaporated to obtain Boc-L-Ab7-D-Tyr(Me)-L-Ile-D-Pro-OH. The resulting compound was dissolved in TFA (5 ml) and left standing on ice for 30 minutes. After the reaction solution was evaporated, the residue was vacuum-dried to obtain the oily title compound (1.15 mg, 1.84 mmol, 97% yield).

EXAMPLE 32

Synthesis of H-L-Ab8-D-Tyr(Me)-L-Ile-D-Pro-OH.TFA

Boc-L-Ab8-D-Tyr(Me)-L-Ile-D-Pro-OBzl (1.44 g, 1.76 mmol) was dissolved in methanol (5 ml) and subjected to catalytic reduction in the presence of 5% Pd-C (150 mg). After 5 hours, the catalyst Pd-C was filtered and the reaction solution was evaporated to obtain Boc-L-Ab8-D-Tyr(Me)-L-Ile-D-Pro-OH. The resulting compound was dissolved in TFA (5 ml) and left standing on ice for 30 minutes. After the reaction solution was evaporated, the residue was vacuum-dried to obtain the oily title compound (1.15 mg, 1.84 mmol, 97% yield).

EXAMPLE 33

Synthesis of H-L-Ab9-D-Tyr(Me)-L-Ile-D-Pro-OH.TFA

Boc-L-Ab9-D-Tyr(Me)-L-Ile-D-Pro-OBzl (1.31 g, 1.58 mmol) was dissolved in methanol (2 ml) and subjected to catalytic hydrogenation in the presence of 5% Pd-C (150 mg). After 12 hours, the catalyst Pd-C was filtered and the reaction solution was evaporated to obtain Boc-L-Ab9-D-Tyr(Me)-L-Ile-D-Pro-OH. This compound was dissolved in TFA (5 ml) and left standing on ice for 30 minutes. After the reaction solution was evaporated, ether/petroleum ether (1:10) was added to the residue for solidification. This was then vacuum-dried to obtain the title compound (905 mg, 1.42 mmol, 90% yield).

EXAMPLE 34

Synthesis of cyclo(-L-Ab6-D-Tyr(Me)-L-Ile-D-Pro-)

H-D-Tyr(Me)-L-Ile-D-Pro-L-Ab6-OH.TFA (778 mg, 1.07 mmol), HATU (616 mg, 1.62 mmol), and DIEA (0.75 ml) were divided into five aliquots and added to DMF (110 ml) every 30 minutes to carry out a cyclization reaction. After 2 hours, the solvent was removed by evaporation. The residue was dissolved in ethyl acetate, successively washed with 10% citric acid, 4% $NaHCO_3$, and saline. The product was dried over $MgSO_4$ and concentrated, and the resulting foam substance was purified by flash silica gel chromatography (4×30 cm, 1% methanol/chloroform) to obtain a colorless oily compound (146 mg) (23%). HPLC retention time: 9.06 min; HRMS (FAB, dithiodiethanol), 579.2197 [M+H], $C_{27}H_{41}O_5N_4{}^{79}Br$ (579.2182).

This time, a cyclic tetrapeptide containing an HOAt adduct transferred by substituting the Ab6 side chain terminus Br, cyclo(-L-A(OAt)6-D-Tyr(Me)-L-Ile-D-Pro-) (167 mg) (27%), was obtained as a foam. HPLC retention time: 8.16 min; HRMS (FAB, dithiodiethanol), 635.3312 [M+H], $C_{32}H_{43}O_6N_8$ (635.3306)

EXAMPLE 35

Synthesis of cyclo(-L-Ab7-D-Tyr(Me)-L-Ile-D-Pro-)

H-L-Ab7-D-Tyr(Me)-L-Ile-D-Pro-OH.TFA (1.15 g, 1.84 mmol), HATU (1.05 g, 2.76 mmol), and DIEA (1.28 ml) were divided into five aliquots and added to DMF (180 ml) every 30 minutes to carry out a cyclization reaction. The product was purified in the same manner as described above, resulting in a foam (700 mg) (64%). HPLC retention time: 9.90 min; HRMS (FAB, dithiodiethanol), 593.2300 [M+H], $C_{28}H_{42}O_5N_4{}^{79}Br$ (593.2339).

EXAMPLE 36

Synthesis of cyclo(-L-Ab8-D-Tyr(Me)-L-Ile-D-Pro-)

H-L-Ab8-D-Tyr(Me)-L-Ile-D-Pro-OH.TFA (512 mg, 0.80 mmol), HATU (455 mg, 1.20 mmol), and DIEA (0.56 ml) were divided into five aliquots and added to DMF (80 ml) every 30 minutes to carry out a cyclization reaction. After 2 hours, the reaction solution was concentrated, dissolved in ethyl acetate, and successively washed with aqueous 10% citric acid solution, aqueous 4% sodium bicarbonate solution, and saturated saline. This was then dried over $MgSO_4$ and concentrated, and the resulting foam substance was purified by flash silica gel chromatography (4×30 cm, 1% methanol/chloroform) to obtain a foam (267 mg) (55%). HPLC retention time: 9.95 min; HRMS (FAB, dithiodiethanol), 607.2501 [M+H], $C_{29}H_{44}O_5N_4{}^{79}Br$ (607.2495).

EXAMPLE 37

Synthesis of cyclo(-L-Ab9-D-Tyr(Me)-L-Ile-D-Pro-)

H-L-Ab9-D-Tyr(Me)-L-Ile-D-Pro-OH.TFA (905 mg, 1.41 mmol), HATU (833 mg, 2.12 mmol), and DIEA (0.64 ml) were divided into five aliquots and added to DMF (150 ml) every 30 minutes to carry out a cyclic reaction. After two hours, the reaction solution was concentrated, dissolved in ethyl acetate, and successively washed with aqueous 10% citric acid solution, aqueous 4% sodium bicarbonate solution, and saturated saline. This was then dried with $MgSO_4$ and concentrated, and the resulting foam substance was purified by flash silica gel chromatography (4×30 cm, 1% methanol/chloroform) to obtain a foam (533 mg) (61%). HPLC retention time: 10.9 min; HRMS (FAB, dithiodiethanol), 621.2625 [M+H], $C_{30}H_{46}O_5N_4{}^{79}Br$ (621.2652).

EXAMPLE 38

Synthesis of cyclo(-L-Am6(Ac)-D-Tyr(Me)-L-Ile-D-Pro-)

Potassium thioacetate (57.6 mg, 0.504 mmol) was added to DMF (0.5 ml) containing cyclo(-L-Ab6-D-Tyr(Me)-L-Ile-D-Pro-) (146 mg, 0.252 mmol), and this was reacted for 3 hours. The reaction solution was concentrated, dissolved in ethyl acetate, and successively washed with aqueous 10% citric acid solution and saturated saline. After drying over $MgSO_4$ and concentrating, the resulting thioester was isolated and purified in the same manner as after the cyclic reaction to obtain an oily substance (114 mg) (79%). HPLC retention time: 9.06 min; HRMS (FAB, dithiodiethanol), 575.2879 [M+H], $C_{29}H_{43}O_6N_4S$ (575.2903).

EXAMPLE 39

Synthesis of cyclo(-L-Am7(Ac)-D-Tyr(Me)-L-Ile-D-Pro-)

Potassium thioacetate (52 mg, 0.452 mmol) was added to DMF (0.5 ml) containing cyclo(-L-Ab7-D-Tyr(Me)-L-Ile-D-Pro-) (133 mg, 0.226 mmol), and this was reacted for 3 hours. The reaction solution was concentrated, dissolved in ethyl acetate, and successively washed with aqueous 10% citric acid solution and saturated saline. After drying over $MgSO_4$ and concentrating, the resulting thioester was isolated and purified to obtain an oily substance (118 mg). (89%). HPLC retention time: 9.90 min; HRMS (FAB, dithiodiethanol), 589.3605 [M+H], $C_{30}H_{45}O_6N_4S$ (589.3060).

EXAMPLE 40

Synthesis of cyclo(-L-Am8(Ac)-D-Tyr(Me)-L-Ile-D-Pro-)

Potassium thioacetate (100 mg, 0.878 mmol) was added to DMF (1 ml) containing cyclo(-L-Ab8-D-Tyr(Me)-L-Ile-D-Pro-) (267 mg, 0.439 mmol), and this was reacted for 3 hours. The reaction solution was concentrated, dissolved in ethyl acetate, and successively washed with aqueous 10% citric acid solution and saturated saline. After drying over $MgSO_4$ and concentrating, the resulting thioester was isolated and purified to obtain an oily substance (222 mg) (84%). HPLC retention time: 9.95 min; HRMS (FAB, dithiodiethanol), 603.3244 [M+H], $C_{31}H_{47}O_6N_4S$ (575.2903).

EXAMPLE 41

Synthesis of cyclo(-L-Am9(Ac)-D-Tyr(Me)-L-Ile-D-Pro-)

Potassium thioacetate (91.4 mg, 0.804 mmol) was added to DMF (0.5 ml) containing cyclo(-L-Ab9-D-Tyr(Me)-L-Ile-D-Pro-) (250 mg, 0.402 mmol), and this was reacted for 3 hours. The reaction solution was concentrated, dissolved in ethyl acetate, and successively washed with aqueous 10% citric acid solution and saturated saline. After drying over $MgSO_4$ and concentrating, the resulting thioester was isolated and purified to obtain an oily substance (190 mg) (77%). HPLC retention time: 10.9 min; HRMS (FAB, dithiodiethanol), 617.3364 [M+H], $C_{32}H_{49}O_6N_4S$ (617.3373).

EXAMPLE 42

Synthesis of cyclo(-L-Am6(-)-D-Tyr(Me)-L-Ile-D-Pro-SS-dimer (SCOP 302)

Methanol (0.5 ml) containing cyclo(-L-Am6(Ac)-D-Tyr(Me)-L-Ile-D-Pro-) (114 mg, 0.198 mmol) was reacted with methanolic ammonia (10 eq.) to remove the acetyl groups. After the solvent was removed by evaporation, the residue was dissolved in DMF (2 ml), to which 1 M $I_2$ (ethanol) (0.2 ml) was added for oxidization. The SS-dimer produced was purified through a Sephadex LH-20 (DMF) column, and then mixed with water to obtain white powder. The yield was 82 mg (78%). HPLC retention time: 11.6 min; HRMS (FAB, dithiodiethanol), 1063.5391 [M+H], $C_{54}H_{79}O_{10}N_8S_2$ (1063.5361).

EXAMPLE 43

Synthesis of cyclo(-L-Am7(-)-D-Tyr(Me)-L-Ile-D-Pro-) SS-dimer (SCOP 304)

Methanol (0.5 ml) containing cyclo (-L-Am7(Ac)-D-Tyr (Me)-L-Ile-D-Pro-) (118 mg, 0.201 mmol) was reacted with methanolic ammonia to remove the acetyl groups of the compounds. The terminal sulfohydryl groups of the compounds were oxidized by adding 1 M $I_2$ (ethanol). After purification, SS-dimer was obtained as white powder. 98 mg (89%) yield. HPLC retention time: 12.3 min; HRMS (FAB, dithiodiethanol), 1091.5684 [M+H], $C_{56}H_{83}O_{10}N_8S_2$ (1091.5674)

EXAMPLE 44

Synthesis of cyclo(-L-Am8(-)-D-Tyr(Me)-L-Ile-D-Pro-SS-dimer (SCOP 306)

Methanol (0.5 ml) containing cyclo(-L-Am8(Ac)-D-Tyr (Me)-L-Ile-D-Pro-) (222 mg, 0.368 mmol) was reacted with methanolic ammonia to remove the acetyl groups of the compounds. The terminal sulfohydryl groups of the compounds were oxidized by adding 1 M $I_2$ (ethanol). After purification, SS-dimer was obtained as white powder. 167 mg (81%) yield. HPLC retention time: 13.0 min; HRMS (FAB, dithiodiethanol), 1119.5961 [M+H], $C_{56}H_{86}O_{10}N_8S_2$ (1119.5987)

EXAMPLE 45

Synthesis of cyclo(-L-Am9(-)-D-Tyr(Me)-L-Ile-D-Pro-SS-dimer (SCOP 308)

Methanol (0.5 ml) containing cyclo(-L-Am9(Ac)-D-Tyr (Me)-L-Ile-D-Pro-) (95 mg, 0.154 mmol) was reacted with methanolic ammonia to remove the acetyl groups of the compounds. The terminal sulfohydryl groups of the compounds were oxidized by adding 1 M $I_2$ (ethanol). After purification, SS-dimer was obtained as white powder. 84 mg (98%) yield. HPLC retention time: 14.2 min; HRMS (FAB, dithiodiethanol), 1147.6307 [M+H], $C_{60}H_{91}O_{10}N_8S_2$ (1147.6300).

EXAMPLE 46

Synthesis of cyclo(-L-Am7(SMEt)-D-Tyr(Me)-L-Ile-D-Pro-) (SS hybrid: SCOP 404)

DMF (0.5 ml) containing cyclo(-L-Am7(Ac)-D-Tyr(Me)-L-Ile-D-Pro-) (270 mg, 0.45 mmol) was reacted with methanolic ammonia (10 eq.) to remove the acetyl groups of the compounds. After ammonia was removed by evaporation, 2-mercaptoethanol (10 eq.) and then 1 M $I_2$ (ethanol) 0.2 ml were added to the residue, causing oxidation. The resulting SS-hybrid was purified by a Sephadex LH-20 (DMF) column and freeze-dried to obtain the title compound as a white powder. The yield was 30 mg (11%). HPLC retention time: 8.9 min; HRMS (FAB, dithiodiethanol), 622.2877 [M], $C_{30}H_{46}O_6N_4S_2$ (622.2859).

EXAMPLE 47

Synthesis of cyclo(-L-Am7(S2Py)-D-Tyr(Me)-L-Ile-D-Pro-) (SS hybrid: SCOP 401)

DMF (1 ml) containing cyclo(-L-Am7(Ac)-D-Tyr(Me)-L-Ile-D-Pro-) (40 mg, 0.07 mmol) was mixed with 2,2'-dithiopyridine (31 mg, 0.14 mmol) and methanolic ammonia (10 eq.) and stirred for 8 hours. After the reaction solution was concentrated, the powder product was purified by flash silica gel chromatography (4×30 cm, 1% methanol/chloroform) to obtain the title compound. The yield was 15 mg (38%). HPLC retention time: 9.6 min; HRMS (FAB, dithiodiethanol), 656.2952 [M+H], $C_{33}H_{45}O_5N_5S_2$ (656.2940).

EXAMPLE 48

Synthesis of cyclo(-L-Am7(S4Py)-D-Tyr(Me)-L-Ile-D-Pro-) (SS hybrid: SCOP 402)

DMF (1 ml) containing cyclo(-L-Am7(Ac)-D-Tyr(Me)-L-Ile-D-Pro-) (100 mg, 0.17 mmol) was mixed with 4,4'-dithiopyridine (75 mg, 0.34 mmol) and methanolic ammonia (20 eq.) and stirred for 8 hours. After the reaction solution was concentrated, the powder product was purified by flash silica gel chromatography (4×30 cm, 1% methanol/chloroform) to obtain the title compound. The yield was 13 mg (13%). HPLC retention time: 6.5 min; HRMS (FAB, dithiodiethanol), 656.2934 [M+H], $C_{33}H_{45}O_5N_5S_2$ (656.2940).

EXAMPLE 49

Synthesis of cyclo(-L-Am7(SEll)-D-Tyr(Me)-L-Ile-D-Pro-) (SS hybrid: SCOP 403)

DMF (2.8 mL) containing 5,5'-dithiobis(2-nitrobenzoic acid) (515 mg, 1.4 mmol) was mixed with dimethylamine (343 mg, 3.0 mmol), DCC (867 mg, 3.0 mmol), and $HOBt.H_2O$ (214 mg, 1.4 mmol), and then stirred for eight hours while cooling on ice. On completion of the reaction, the reaction solution was concentrated, dissolved in ethyl acetate, and successively washed with an aqueous 10% citric acid solution, an aqueous 4% sodium bicarbonate solution, and saturated saline. After drying over $MgSO_4$, ethyl acetate was removed by evaporation. The residue was vacuum-dried and purified using flash silica gel chromatography (4×30 cm, 1% methanol/chloroform) to obtain 5,5'-dithiobis(2-nitrobenzoic acid dimethylamide).

DMF (2 ml) containing cyclo(-L-Am7(Ac)-D-Tyr(Me)-L-Ile-D-Pro-) (130 mg, 0.22 mmol) was mixed with 5,5'-dithiobis(2-nitrobenzoic acid dimethylamide) (198 mg, 0.44 mmol) and methanolic ammonia (10 eq.), and then stirred for 6 hours. The reaction solution was concentrated, dissolved in a small amount of DMF, and purified by HPLC (column: YMC-Pack ODS-A 10×250 mm) to obtain the title compound. The yield was 13 mg (9.3%). HPLC retention time: 9.5 min; HRMS (FAB, dithiodiethanol), 771.3201 [M+H], $C_{37}H_{50}O_8N_6S_2$ (771.3210).

EXAMPLE 50

Synthesis of cyclo(-L-Am7(SMe)-D-Tyr(Me)-L-Ile-D-Pro-) (SCOP 405)

DMF (1 ml) containing cyclo(-L-Ab7-D-Tyr(Me)-L-Ile-D-Pro-) (118 mg, 0.2 mmol) was mixed with 4-methoxybenzylmercaptan (0.056 ml, 0.4 mmol) and triethylamine (0.07 ml, 0.5 mmol) and reacted at a room temperature for 2 hours. The produced cyclo(-L-Am7(Mb)-D-Tyr(Me)-L-Ile-D-Pro-) was extracted with ethyl acetate, purified, and then reacted with dimethyl(methylthio)sulfonium tetrafluoroborate (0.9 mmol, 176 mg) in methanol (18 ml) at room temperature for 2 hours. The reaction solution was concentrated, dissolved in chloroform, and purified by silica gel chromatography (2×25 cm, 2% methanol/chloroform) to obtain the target product. The yield was 69 mg (65%). TLC Rf: 0.90 ($CHCl_3$/MeOH=19/1). HPLC retention time: 12.28 min; HR-FAB+ MS: 593.2777 (calcd.: 592.2753, composition: $C_{29}H_{44}O_5N_4S_2$, matrix: 2,2'-ditihidiethanol).

EXAMPLE 51

Measurement of HDAC Inhibition Activity

Figure 5:
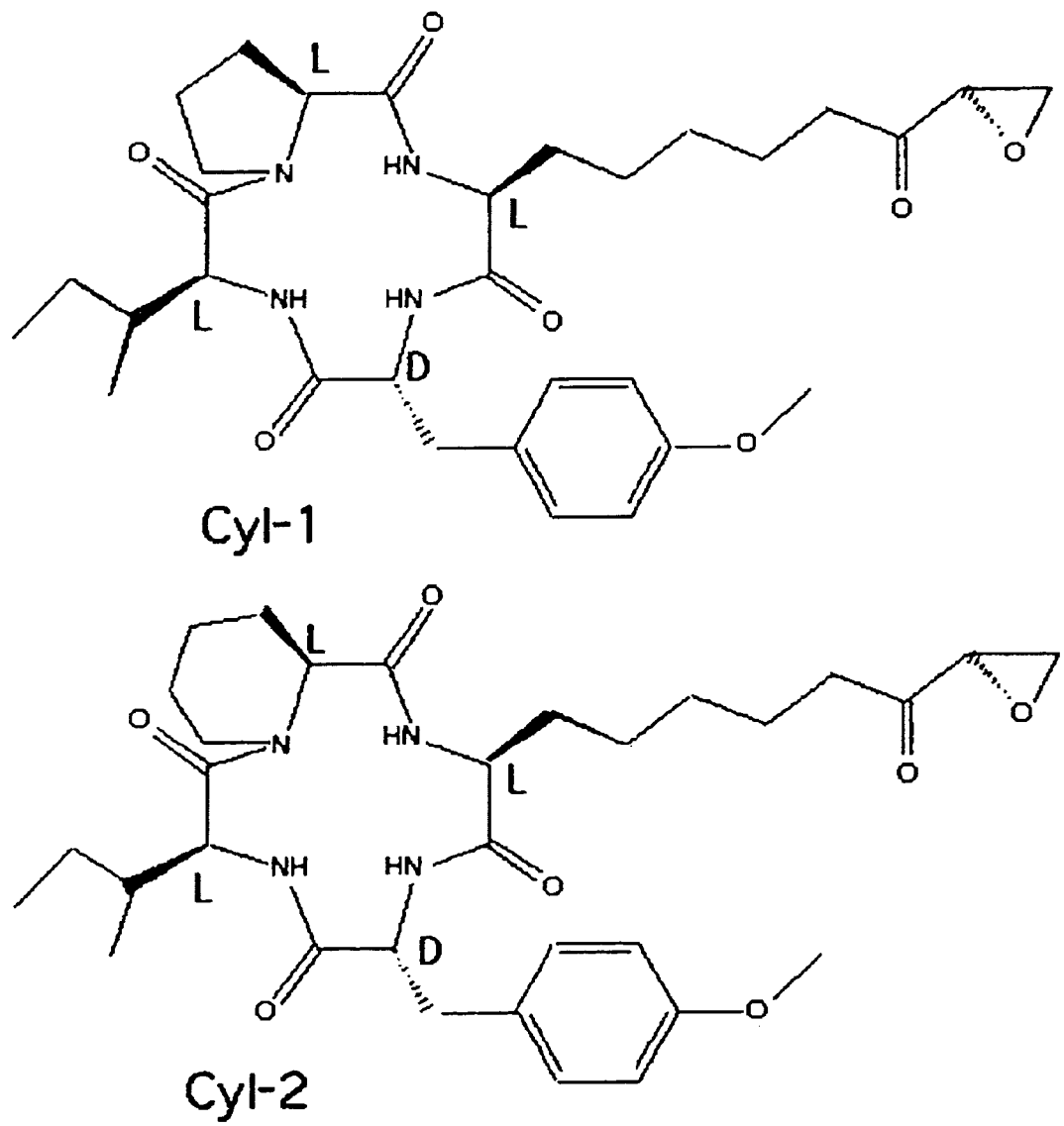
FIG. 5 shows the steric conformation of natural Cyl-1 and Cyl-2.

In this Example, the HDAC inhibition activity of SCOP was measured. FIG. 1 to FIG. 4 show lists of the structures of the sulfur-containing cyclic peptides (SCOP) whose activity was measured. The conformation and number of carbon chains until the active groups of the cyclic tetrapeptide structures were investigated based on natural HDAC inhibitors, Cyl-1 and Cyl-2, as shown in FIG. 5 (Furumai et al. (2001) Proc. Natl. Acad. Sci. USA, 98, 87-92).

The steric conformation of natural Cyl-1 and Cyl-2 is LDLL, however those with LDLD conformation were also investigated. In the following experimental results, DTT is coexisted for X=H, for the purpose of cutting disulfide bonds.

To measure HDAC inhibition activity, an HDAC solution was prepared as described below. $1\times10^7$ of 293T cells were plated on to a 100-mm dish and, after 24 hours, transfected with vectors (1 μg) expressing human HDAC1 and HDAC4 or mouse HDAC6, using LipofectAmine 2000 reagent (Life Technologies, Inc. Gaithersburg, Md.). The above-mentioned pcDNA3-HD1 was used as a vector expressing human HDAC1 (Yang, W. M., Yao, Y. L., Sun, J. M., Davie, J. R. & Seto, E. (1997) J. Biol. Chem. 272, 28001-28007). pcDNA3.1 (+)-HD4 was used as a vector expressing human HDAC4 (Fischle, W., Emiliani, S., Hendzel, M. J., Nagase, T., Nomura, N., Voelter, W. & Verdin, E. (1999) J. Biol. Chem. 274, 11713-11720). pcDNA-mHDA2/HDAC6 was used as a vector expressing mouse HDAC6 (Verdel, A. & Khochbin, S. (1999) J. Biol. Chem. 274, 2440-2445). The vectors were introduced for five hours in OPTI-MEM. The medium was then replaced with Dulbecco's modified Eagle's medium (DMEM), and incubated for 19 hours. The cells were washed with PBS, suspended in lysis buffer (50 mM Tris-HCl (pH7.5), 120 mM NaCl, 5 mM EDTA, and 0.5% Nonidet P-40), and sonicated. The supernatant was collected by centrifugation and nonspecific protein was removed using Protein A/G plus agarose beads (Santa Cruz Biotechnologies, Inc.). Anti-FLAG M2 antibodies (Sigma-Aldrich, Inc.) were added to the supernatant of cells expressing HDAC1 or HDAC4. Anti-HA antibodies (clone 3F10, Roche Molecular Biochemicals) were added to the supernatant of cells expressing HDAC6. Reaction in the respective mixtures was carried out at 4° C. for one hour. The resulting reaction mixtures were independently mixed with agarose beads and further reacted at 4° C. for one hour. The agarose beads were washed three times with lysis buffer and then washed once with HD buffer (20 mM Tris-HCl (pH8.0), 150 mM NaCl, 10% glycerol, and a complete protease inhibitor cocktail (Boehringer Mannheim, Germany)). The protein solution, referred to as "HDAC reaction solution", that had bonded to the agarose beads was recovered by incubation with FLAG peptide (40 μg) (Sigma-Aldrich, Inc.) or HA peptide (100 μg) in an HD buffer (200 μl) at 4° C. for one hour. The HDAC reaction solution was used for determining HDAC inhibition activity as shown below.

In vitro HDAC inhibition activity was evaluated as follows: A test compound was dissolved in DMSO and adjusted to 10 mM. This was used as an inhibitor stock solution. As a positive control, Tricostatin A (TSA), known as an HDAC inhibitor, was dissolved in DMSO to obtain a 10 mM stock solution. Measurement was carried out by incubating each of the above-mentioned HDAC solutions and a solution of acetylated histone substrate labeled with [$^3$H] at 37° C. for 15 minutes (100 μl reaction volume) in the presence of a test compound or control TSA. These reactions were stopped by adding 10 μl HCl. The [$^3$H] acetic acid excised by the enzyme reaction was extracted with ethyl acetate and subjected to radioactive dose measurement. As a negative control, the same procedure was carried out in which no inhibitor was added to the reaction system. The inhibition activity was expressed as a 50% inhibition concentration ("IC50 (nM)") of the HDAC activity in the negative control (Tables 1 to 4).

The HDAC inhibition activity in vivo was measured using p21 promoter-inducing activity as an index, as shown below. The MFLL-9 cells employed for the experiments stably maintained fusion genes of human wild-type p21 promoter and luciferase (Dr. B. Vogelstein). Using phenol red-free DMEM medium comprising 10% FBS, cultivation was carried out in a steam-saturated incubator at 37° C. with 5% carbon dioxide. The MFLL-9 cells were plated at a density of 85,000 cells/well on a 96-well microtiter plate, each in 99 μl of the above-mentioned medium. These were then cultivated for six hours. One μl of test compound solution was added to each well, which was then cultured for another 18 hours. TSA was used as the positive control compound with p21 promoter-inducing activity, which results from HDAC inhibition activity.

The intensity of luminescence caused by the product of the enzyme reaction for intracellular luciferase expression was measured using Luc Lite (Packard BioScience Company). A group in which test compounds were not added was used as a negative control group. The values measured for this group were used as a standard. The activities for each concentration of added test compound were expressed relative to the above-mentioned standard value, 1. The test compound activity intensities were compared using the concentrations ("EC50 (nM)") corresponding to 50% of the maximum active values for TSA (Tables 1 to 4).

TABLE 1

X = H (coexisting with DTT)

| Inhibitor | IC50 (nM) | | | P21 Promoter | | Number of |
|---|---|---|---|---|---|---|
| SCOP No. | HDAC1 | HDAC4 | HDAC6 | EC50 (nM) | Conformation | Carbon Chains |
| 148 | 81.4 | 17.0 | >500000 | 6720 | Cyl1 (LDLL) | C5 |
| 149 | 2.37 | 5.22 | 44300 | 596 | Cyl2 (LDLL) | C5 |
| 150 | 2.10 | 4.26 | 5560 | 504 | Cyl2 (LDLD) | C5 |
| 151 | 932 | 7340 | 28500 | >100000 | Cyl1 (LDLD) | C4 |
| 152 | 4.60 | 2.06 | 1400 | 309 | Cyl1 (LDLD) | C5 |
| 153 | 9.13 | 91.0 | 8050 | 9850 | Cyl1 (LDLD) | C6 |
| 154 | 38.1 | 99.2 | 2470 | 31400 | Cyl1 (LDLD) | C7 |

As the in vitro inhibition activity and in vivo P21 promoter activity of Table 1 shows, LDLD isomers were found to have higher activities than LDLL isomers which are in a natural conformation. In addition, C5 was shown to be most preferable as the number of carbon chains until the active thiol group.

TABLE 2

X = a compound comprising the left conformation (homodimer)

| Inhibitor | IC50 (nM) | | | P21 Promoter | | Number of Carbon |
|---|---|---|---|---|---|---|
| SCOP No. | HDAC1 | HDAC4 | HDAC6 | EC50 (nM) | Conformation | Chains |
| 296 | 763 | 222 | >500000 | 7730 | Cyl1 (LDLL) | C5 |
| 298 | 114 | 33.7 | 418000 | 5800 | Cyl2 (LDLL) | C5 |
| 300 | 61.1 | 36.2 | 255000 | 7370 | Cyl2 (LDLD) | C5 |
| 302 | 7200 | >500000 | >500000 | >100000 | Cyl1 (LDLD) | C4 |
| 304 | 142 | 145 | >500000 | 341 | Cyl1 (LDLD) | C5 |
| 306 | 153 | 319 | 1320000 | 847100000 | Cyl1 (LDLD) | C6 |
| 308 | 983 | 505 | 745000 | 235000 | Cyl1 (LDLD) | C7 |

As for the case of X=H, with respect to the homodimers, it was shown that LDLD isomers have higher activities than LDLL isomers which are in a natural conformation, and that C5 is the most preferable number of carbon chains until the active thiol group.

TABLE 3

X = a low molecular-weight compound (hybrid)

| Inhibitor | IC50 (nM) | | | P21 Promoter | |
|---|---|---|---|---|---|
| SCOP No. | HDAC1 | HDAC4 | HDAC6 | EC50 (nM) | Conformation |
| 401 | NT | NT | NT | 1360 | 152 + 2-Pyridine |
| 402 | 6.76 | 68.3 | 1610 | 1310 | 152 + 4-Pyridine |
| 403 | 21.5 | 18.9 | 6080 | 1800 | 152 + Ellman's reagent |
| 404 | 217 | 355 | 201000 | 1360 | 152 + Mercaptoethanol |
| 405 | 119 | 405 | 191 | 3260 | 152 + Methylmercaptane |
| 401/DTT | NT | NT | NT | 815 | |
| 402/DTT | 0.553 | 1.12 | 2010 | 470 | |
| 403/DTT | 1.15 | 1.53 | 4730 | 748 | |
| 404/DTT | 2.44 | 13.0 | 15400 | 754 | |

"NT" means that no test was carried out.

Even hybrid bodies of SCOP 152 and low molecular-weight compounds were shown to have inhibition activity.

TABLE 4

| | Positive control (TSA) | | | |
|---|---|---|---|---|
| Inhibitor | IC50 (nM) | | | P21 Promoter |
| TSA | HDAC1 | HDAC4 | HDAC6 | EC50 (nM) |
| TSA | 19.2 | 68.3 | 27.2 | 445 |

According to the above results, LDLD isomers have higher activities than LDLL isomers in their natural conformation. In addition, C5 was found to be the most preferable number of carbon chains until the active thiol group. Furthermore, since the HDAC6 inhibition activity was significantly low, the compounds were confirmed to comprise enzyme subtype-selective inhibition activity. On an enzymatic level, the present compounds showed high HDAC inhibition activity when they were thiols (X=H) coexisting with DTT. However, on a cellular level, even those X=left structure or X=low molecular-weight compounds showed high activity. This suggests that thiol groups were exposed and thus activated by reducing the disulfides incorporated into cells using intracellular reducing forces.

Next, since it was possible that DTT had some effect, an experiment was carried out using purified SCOP 152, under DTT-free conditions.

TABLE 5

| | IC50 (nM) | | | P21 Promoter |
|---|---|---|---|---|
| Inhibitor | HDAC1 | HDAC4 | HDAC6 | EC50 (nM) |
| 152 | NT | NT | NT | 3510 |

"NT" means that no test was carried out.

The EC50 value increased compared to when DTT was present. DTT's existence was thought to reduce the pH of the culture medium, causing a change in monomer stability. Alternatively, it may be also possible that DTT served as a protection group. The following experiment was carried out using purified SCOP 152 under the DTT-free conditions.

EXAMPLE 52

Measurement of in vivo HDAC Inhibition Activity

Figure 6:
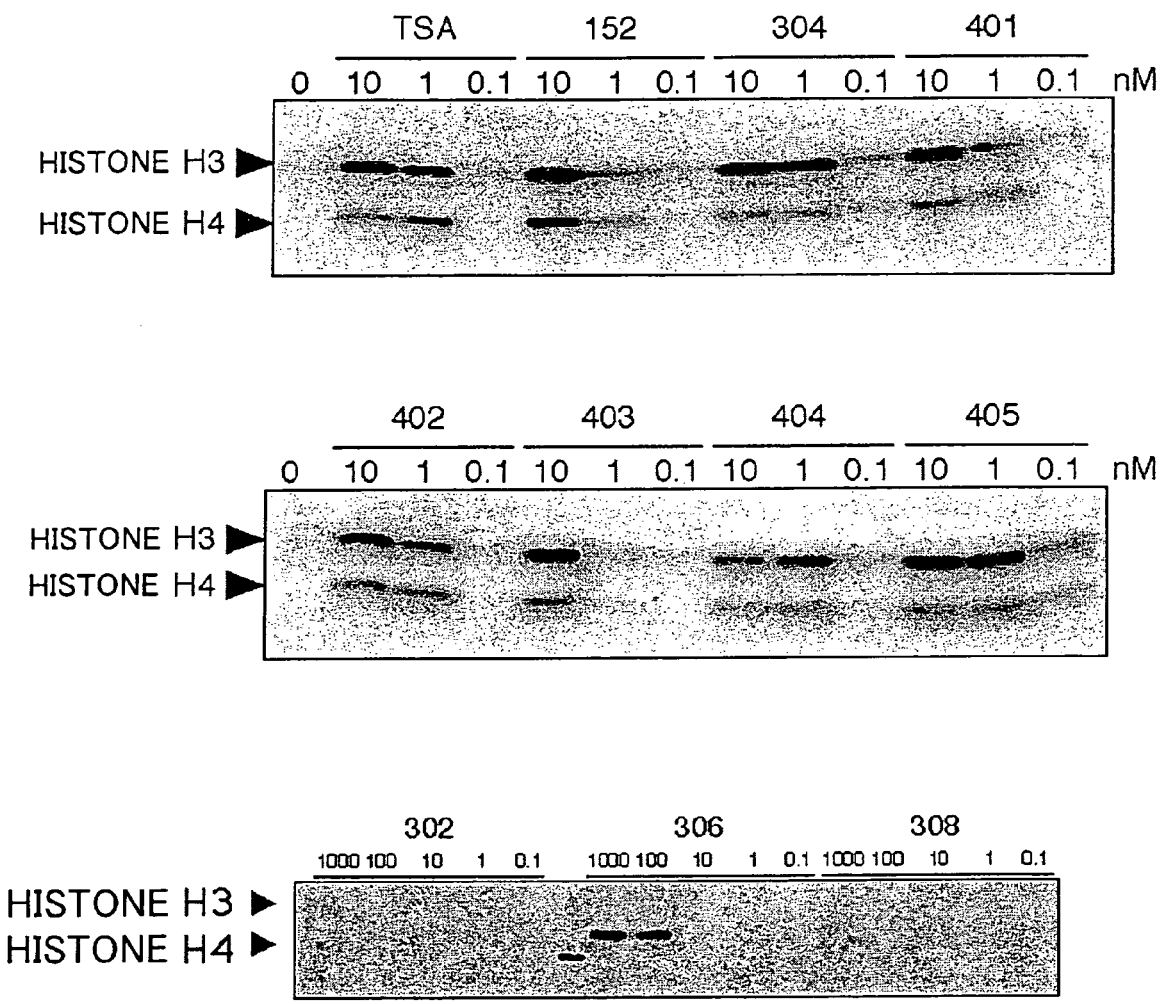
FIG. 6 shows photographs of the results of measuring intracellular histone acetylation level by Western blot analysis using anti-acetylated lysine antibodies.

Histone acetylation levels were measured by: (i) reacting a test compound with HeLa cells; and (ii) confirming the histone acetylation level by Western blotting using anti-acetylated lysine antibodies. Specifically, human uterine cancer cells (HeLa) were cultured in a DMEM medium comprising 10% FBS at 37° C. in the presence of 5% carbon dioxide in a steam-saturated incubator. Two ml of the cells at a density of 15,000 cells/ml were plated onto a 6-well plate and cultured for 18 hours. Test compound solution was added to each culture and successively cultured for another six hours. The cells were washed with PBS, suspended in a lysis buffer (50 mM Tris-HCl (pH7.5), 120 mM NaCl, 5 mM EDTA, 0.5% Nonidet P-40), and then sonicated. The supernatant was collected by centrifugation, mixed with SDS buffer, and left at 100° C. for five minutes. The resulting sample was subjected to electrophoresis on a 15% SDS gel and transferred to a membrane film. This was treated with primary antibody "AKL5C1" (Japan Energy), and secondary antibody "anti-mouse" (LIFE SCIENCE), and then acetylation bands were detected by ECL (amersham pharmacia biotech) (FIG. 6). The concentration unit of the compounds shown in FIG. 6 is "nM".

As shown in FIG. 6, the inhibition tendencies shown were the same as the results (EC50) of P21 promoter-inducing activity. C5 was the most preferable number of carbon chains until the active thiol group.

EXAMPLE 53

Cytotoxicity Test

Human normal lung cells (TIG-3) and human uterine cancer cells (HeLa) were used to test SCOP cytotoxicity. These TIG-3 and HeLa cells were cultured in a DMEM medium comprising 10% FBS at 37° C. in the presence of 5% carbon dioxide in a steam-saturated incubator. The TIG-3 and HeLa cells were plated in 100 μl/well of the above-described medium on a 96-well microtiter plate, at a density of 30,000 cells/well and 10,000 cells/well respectively. This was then cultured for 18 hours. Test compound solution diluted with medium was added to each well and culture was continued for another 48 hours.

30 μl of supernatant from each well was transferred to another 96-well microtiter plate (A), and the remaining supernatant was discarded. 100 μl of 0.5% Triton-X/PBS was added to each well to lyse the cells, and 30 μl was then transferred to each respective well of another 96-well microtiter plate (B). 30 μl of LDH-Cytotoxic Test (Wako) substrate solution was added to each well of these 96-well microtiter plates A and B, causing a color reaction. Once the color reaction was sufficiently progressed, it was stopped by adding 60 μl of a quenching solution. Color intensity was measured at OD560 nm using a microplate reader (Softmax). [A/(A+B)] was calculated as the free-LDH ratio. Inhibition activity was shown as LD50 when the free-LDH ratio was 50%. The higher the activity value for cancer-cell-selective cell damage (LD50 for normal cells/LD50 for cancer cells), the more that cancer-cell-selective apoptosis was induced.

TABLE 6

| | LD50 (nM) | | Cancer-Cell-Selective |
|---|---|---|---|
| Inhibitor | HeLa | TIG-3 | Cytotoxicity |
| TSA | 41.4 | 1580 | 38.2 |
| SCOP 152 | 370 | 6780 | 18.3 |
| SCOP 304 | 151 | 3471 | 23.0 |
| SCOP 402 | 1170 | 13300 | 11.4 |
| SCOP 405 | 179 | 7900 | 44.1 |
| SCOP 304/DTT | 47.1 | 1190 | 25.2 |
| SCOP 402/DTT | 161 | 4460 | 27.8 |

As shown in Table 6, the compounds of the present invention were confirmed to have intense cancer-cell-selective cytotoxicity that is as effective as TSA.

EXAMPLE 54

Evaluation of Stability

The stability of SCOP 152, SCOP 304, and SCOP 402 in serum was evaluated by the method shown below: 1 μl of 10 mM SCOP 152, SCOP 304, and SCOP 402 was added to 99 μl FCS, and incubated at 37° C. Each hour, NaCl in a sufficient amount for saturation and 1 ml of ethyl acetate were added to each mixture. After extraction, from 800 μl of the ethyl acetate phase, the ethyl acetate was distilled off, and then 100 µl of DMSO was added to the residue. The resulting solution was further diluted ten times with DMSO and used to measure p21 promoter inducing activity. Activity at incubation time zero was taken as 100%, and activities were compared (FIG. 7).

Figure 7:
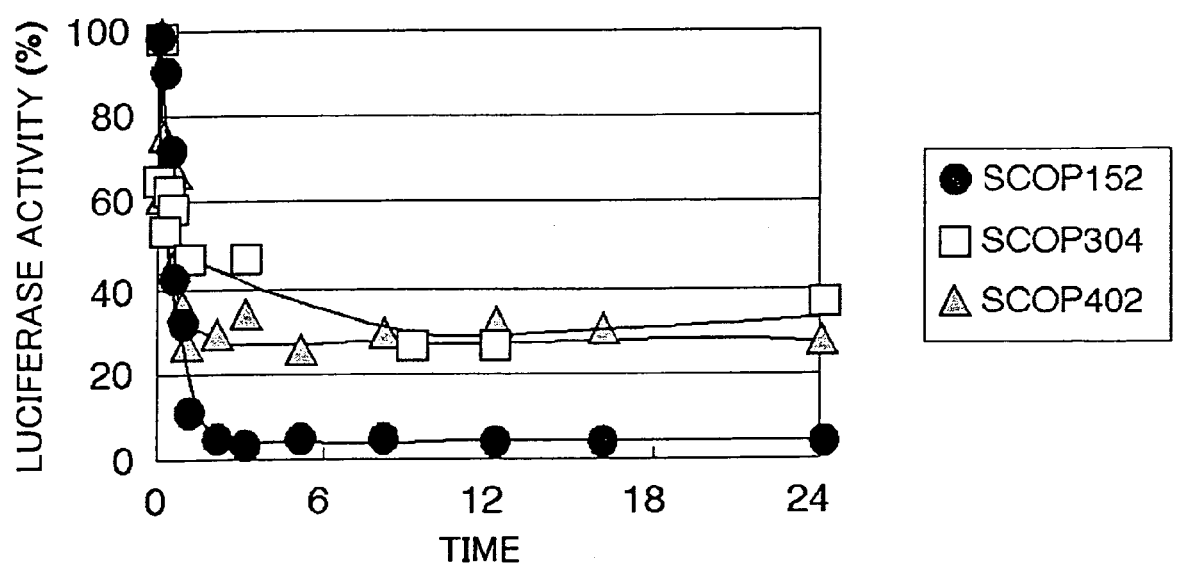
FIG. 7 shows the results of evaluating the stability of SCOP 152, SCOP 304, and SCOP 402 in serum.

As shown in FIG. 7, SCOP 304 and SCOP 402 were able to stably retain activity in serum for longer than SCOP 152. This stability was thought to be improved by the protection of thiol groups.

Figure 8:
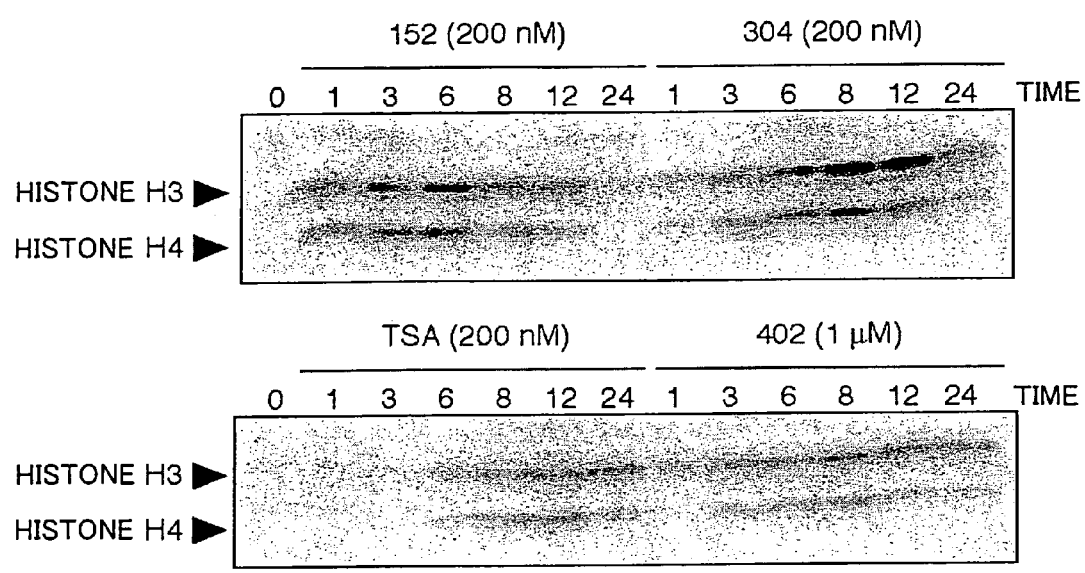
FIG. 8 shows photographs of the results of evaluating the stability of SCOP 152, SCOP 304, and SCOP 402 on a cellular level.

Next, in vivo stability was investigated based on histone acetylation levels. HeLa cells were treated with each compound and then histone acetylation level was analyzed by Western blotting using an anti-acetylated lysine antibody (FIG. 8). Specifically, human uterine cancer cells (HeLa) were cultured in DMEM medium comprising 10% FBS at 37° C. with 5% carbon dioxide in a steam-saturated incubator. Two ml of the cells were plated at a density of 15,000 cells/ml in a 6-well plate, and cultured for 18 hours. 200 nM of test compound solutions comprising TSA, SCOP 152 and SCOP 304, and 1 µM test compound SCOP 402 solution were added, and culture was continued for an appropriate time. The cells were washed with PBS, suspended in a lysis buffer (50 mM Tris-HCl (pH7.5), 120 mM NaCl, 5 mM EDTA, and 0.5% Nonidet P-40), and then sonicated. Each supernatant was collected by centrifugation, mixed with a SDS buffer, and treated at 100° C. for five minutes. The resulting sample was subjected to electrophoresis on a 15% SDS gel and transferred to a membrane film. After treatment with primary antibody "AKL5C1" (Japan Energy), and secondary antibody "anti-mouse" (LIFE SCIENCE), ECL (amersham pharmacia biotech) treatment was carried out and acetylation bands were detected.

The compounds of the present invention showed intense inhibition activity towards HDAC1 and HDAC4, but scarcely any inhibition activity towards HDAC6. HDAC6 is highly expressed in the testes and such, and is predicted to be relevant to normal tissue differentiation. However, HDAC6 has not been found to be related to carcinogenesis. Therefore, inhibition of HDAC6 may lead to side effects. Since the compounds of the present invention have extremely weak HDAC6 inhibition activity, as well as sub-type selectivity, which TSA does not have, they are useful as novel inhibitors. Furthermore, the tetrapeptide backbone structure of the compounds of the present invention can be easily changed, suggesting further selectivity can be conferred.

INDUSTRIAL APPLICABILITY

As described above, the compounds of the present invention show strong selective inhibitory activity towards HDAC1 and HDAC4. Accordingly, the compounds of the present invention may be useful as pharmaceutical agents for treating or preventing diseases associated with HDACs, particularly HDAC1 and HDAC4. The methods for producing the compounds of the present invention are carried out by using 2-amino-n-haloalkanoic acid as a raw material to easily synthesize various types of compounds. Consequently, use of the production methods of the present invention is expected to contribute to the development of HDAC inhibitors with greater selectivity.

The invention claimed is:

1. A compound represented by the following formula (1):

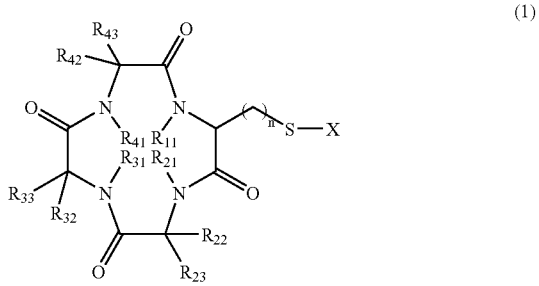

wherein, $R_{11}$, $R_{21}$, $R_{22}$, $R_{31}$, $R_{32}$, and $R_{43}$ independently denote hydrogen or methyl; $R_{23}$, and $R_{33}$, denote p-methoxybenzyl and sec-butyl, respectively, the pairs of $R_{41}$ and $R_{42}$ denotes a cyclic structure formed from the binding of a linear alkylene group with a three-carbon main chain; X denotes pyridine-2ylthio; and n is 5.

2. An in vitro histone deacetylase inhibitor composition that comprises the compound of claim 1 as an active ingredient and a carrier.

* * * * *

UNITED STATES PATENT AND TRADEMARK OFFICE
CERTIFICATE OF CORRECTION

PATENT NO. : 7,488,712 B2
APPLICATION NO. : 10/505380
DATED : February 10, 2009
INVENTOR(S) : Yoshida et al.

It is certified that error appears in the above-identified patent and that said Letters Patent is hereby corrected as shown below:

Title Page, item 56 References Cited, Foreign Patents, below "JP 2000-256397 9/2000" please delete "JP 2000256397 9/2000";

Column 36, line 36 (Claim 1), plesase delete "pairs" and insert --pair-- therefor.

Signed and Sealed this

Fourteenth Day of July, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,488,712 B2 | Page 1 of 1 |
| APPLICATION NO. | : 10/505380 | |
| DATED | : February 10, 2009 | |
| INVENTOR(S) | : Yoshida et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 375 days Delete the phrase "by 375 days" and insert -- by 877 days --

Signed and Sealed this

Sixth Day of April, 2010

David J. Kappos
*Director of the United States Patent and Trademark Office*